(12) United States Patent
Mills

(10) Patent No.: US 9,801,581 B2
(45) Date of Patent: Oct. 31, 2017

(54) DEVICES, SYSTEMS AND METHODS FOR DETECTING A BILATERAL DIFFERENTIAL IN OLFACTORY THRESHOLD FOR PURE ODORANTS

(71) Applicant: Inspired Technologies, Inc., LeSueur, MN (US)

(72) Inventor: Gregory B. Mills, Kansas City, KS (US)

(73) Assignee: Inspired Technologies, Inc., LeSueur, MN (US)

( * ) Notice: Subject to any disclaimer, the term of this patent is extended or adjusted under 35 U.S.C. 154(b) by 0 days.

(21) Appl. No.: 14/282,622

(22) Filed: May 20, 2014

(65) Prior Publication Data
US 2015/0112161 A1  Apr. 23, 2015

Related U.S. Application Data

(60) Provisional application No. 61/894,210, filed on Oct. 22, 2013, provisional application No. 61/931,148, filed on Jan. 24, 2014.

(51) Int. Cl.
*A61B 5/00* (2006.01)
*A61B 5/087* (2006.01)

(52) U.S. Cl.
CPC .......... *A61B 5/4011* (2013.01); *A61B 5/0875* (2013.01); *A61B 5/4088* (2013.01)

(58) Field of Classification Search
CPC .......... A61B 5/4011; A61B 2560/0431; A61B 5/0051; A61M 2021/0016
See application file for complete search history.

(56) References Cited

U.S. PATENT DOCUMENTS 3,885,550 A * 5/1975 MacLeod ........... G01N 33/0001
                                                    600/303
4,265,248 A   5/1981 Chuiton et al.
(Continued)

FOREIGN PATENT DOCUMENTS

| WO | WO2006/135368 | 12/2006 |
|----|---------------|---------|
| WO | 2011/035284 | 3/2011 |
| WO | WO2013/150446 | 10/2013 |

OTHER PUBLICATIONS

International Preliminary Report on Patentability, dated May 6, 2016 for International PCT Application No. PCT/USZ014/061574, filed Oct. 21, 2014.
(Continued)

*Primary Examiner* — Patricia Mallari
*Assistant Examiner* — Michael Catina
(74) *Attorney, Agent, or Firm* — Barnes & Thornburg LLP; Jeffrey R. Stone

(57) ABSTRACT

The present system is directed in various embodiments to devices, systems and methods for detection, evaluation and/or monitoring olfactory dysfunction by measuring and determining the patient's olfactory detection threshold for the left and the right nostril. More specifically, the present invention relates to devices, systems and methods for detecting an asymmetric differential in a patient's olfactory detection threshold (left vs right nostril) which, when present, may be used as a device to detect, diagnose and/or monitor olfactory deterioration resulting from certain neurodegenerative disorders such as Alzheimer's disease.

13 Claims, 28 Drawing Sheets

(56) References Cited

U.S. PATENT DOCUMENTS

| | | | |
|---|---|---|---|
| 4,934,386 | A | 6/1990 | Walker et al. |
| 6,325,475 | B1 * | 12/2001 | Hayes ............... A61B 5/00 |
| | | | 128/203.11 |
| 6,467,332 | B1 | 10/2002 | Bertschi et al. |
| 6,957,038 | B1 | 10/2005 | Gartner et al. |
| 7,007,694 | B2 | 3/2006 | Aylsworth et al. |
| 8,429,950 | B2 | 4/2013 | Wright |
| 8,469,293 | B2 | 6/2013 | Doty et al. |
| 2005/0192482 | A1 | 9/2005 | Carpenter et al. |
| 2007/0277824 | A1 | 12/2007 | Aylsworth et al. |
| 2008/0223953 | A1 * | 9/2008 | Tomono ............ A01M 1/205 |
| | | | 239/102.2 |
| 2010/0056946 | A1 * | 3/2010 | Holmes ............ A61B 5/7267 |
| | | | 600/549 |
| 2011/0030450 | A1 | 2/2011 | Wright |
| 2012/0078065 | A1 | 3/2012 | De Lemos et al. |
| 2012/0184828 | A1 | 7/2012 | Lundstrom et al. |
| 2013/0012828 | A1 | 1/2013 | Aylsworth |
| 2014/0316485 | A1 * | 10/2014 | Ackermann ...... A61N 1/36046 |
| | | | 607/53 |

OTHER PUBLICATIONS

European Extended Search Report from related EP application No. 14855407.4, dated May 2, 2017.
Monique A.M. Smeets et al.: "Seeing occupational exposure limits in humans: contributions from the field of experimental psychology", International Archives of Occupational and Environmental Health, Springer, Berlin, DE, vol. 79, No. 4, May 1, 2006 (May 1, 2006), pp. 299-307, XP019343393, ISSN: 1432-1246, DOI: 10.1007/S00420-005-0053-8, abstract, p. 300, col. 2-p. 303, col. 2.

* cited by examiner

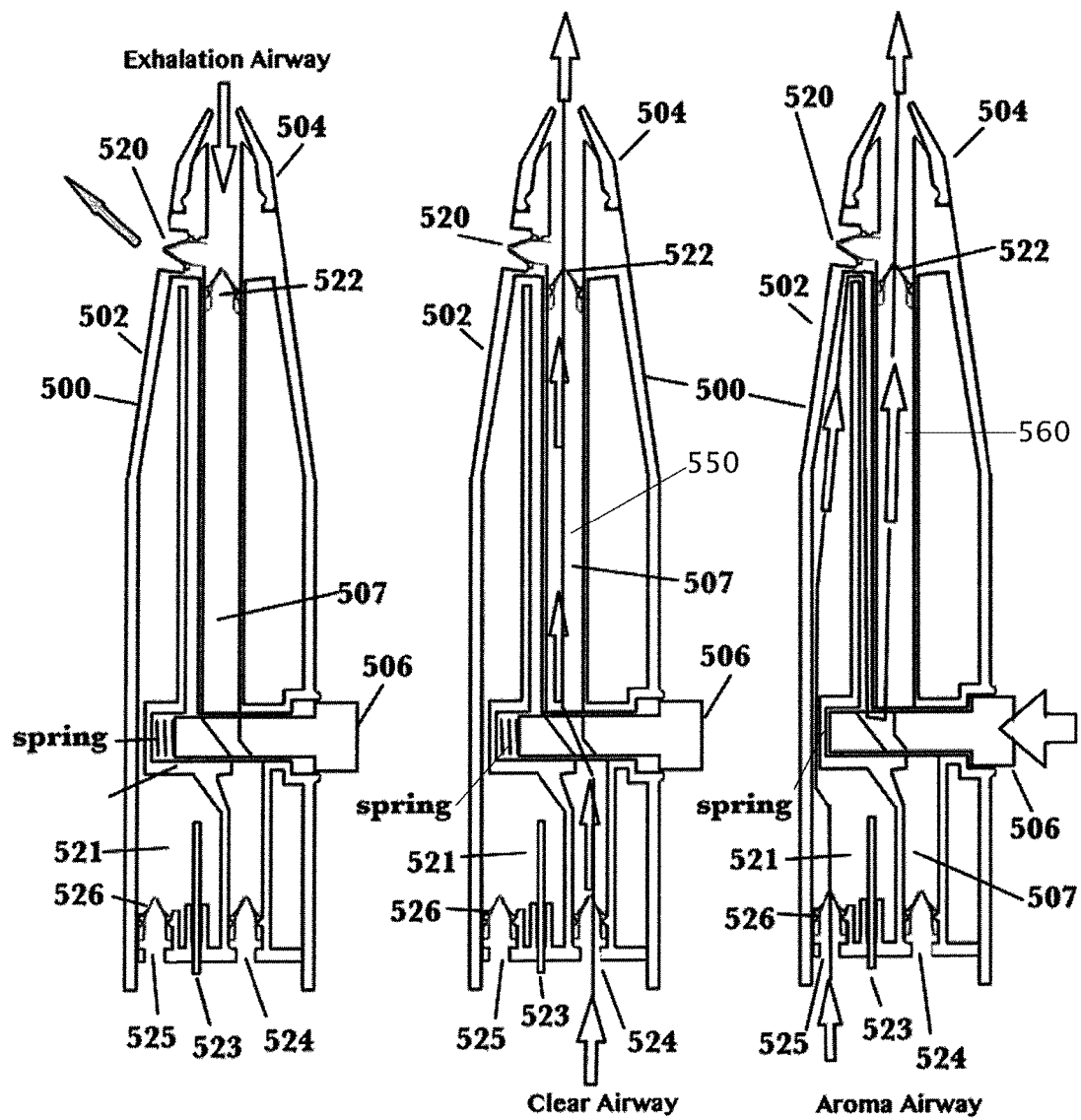

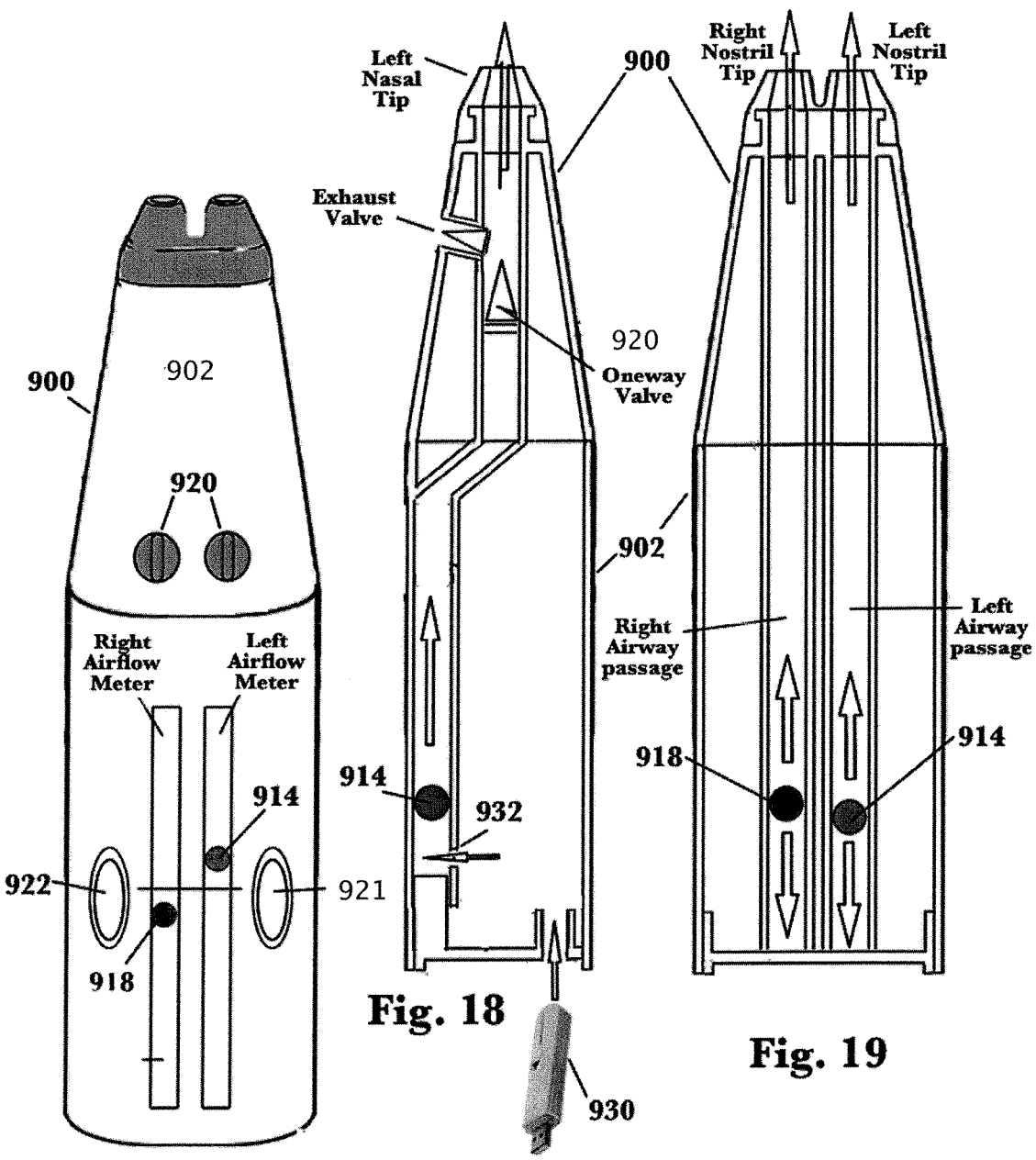

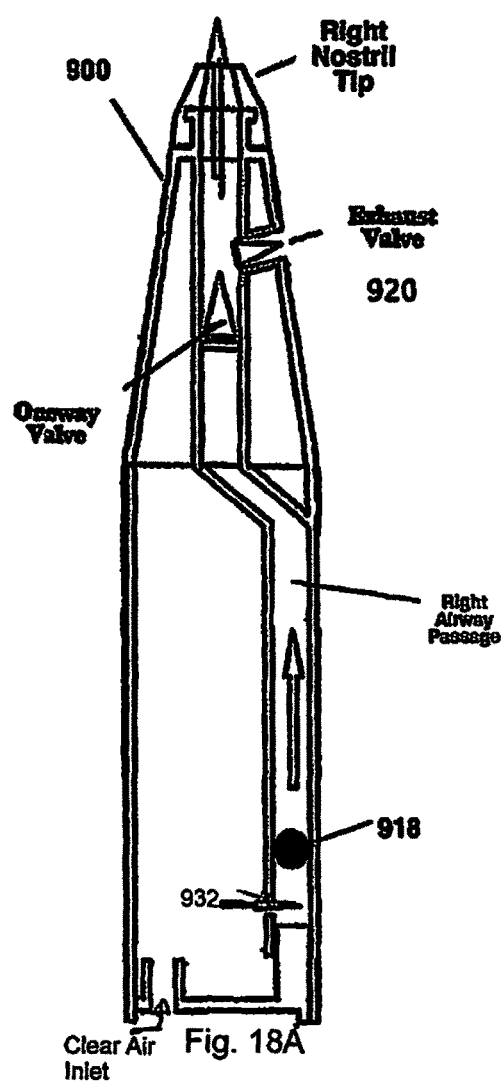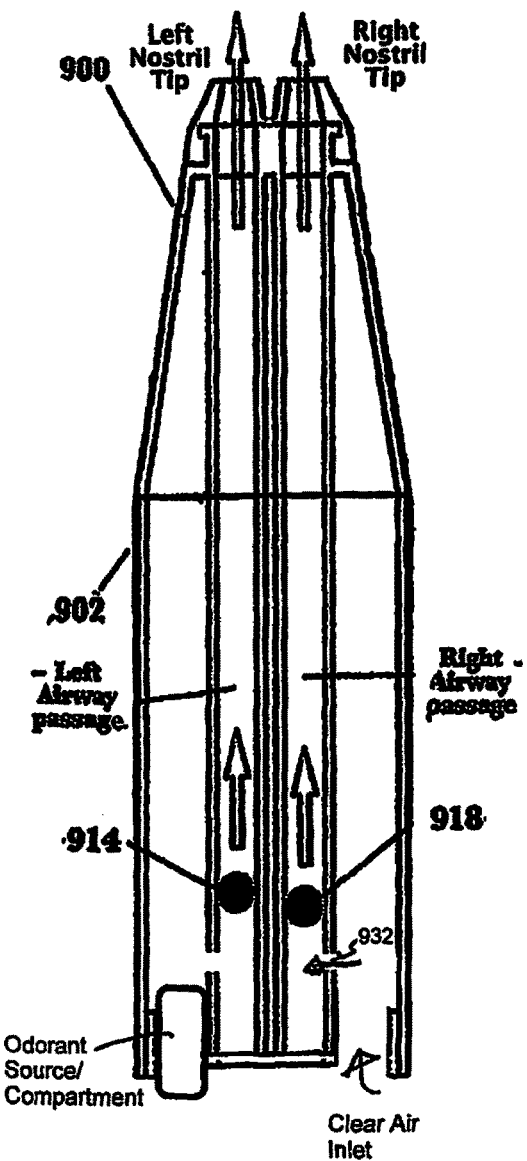
Fig. 18A Right side view
Fig. 19A

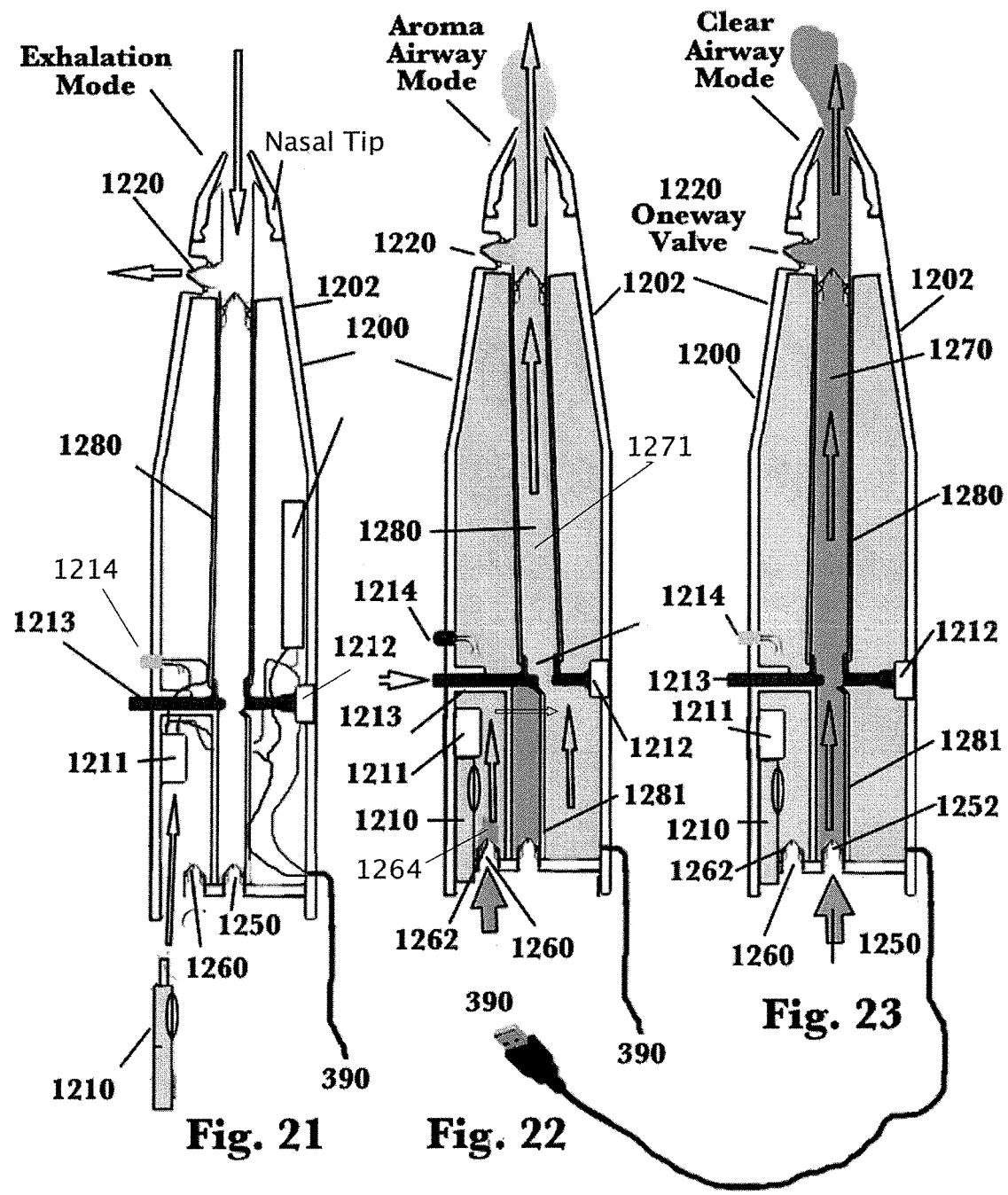

Fig. 31

DEVICES, SYSTEMS AND METHODS FOR DETECTING A BILATERAL DIFFERENTIAL IN OLFACTORY THRESHOLD FOR PURE ODORANTS

CROSS-REFERENCE TO RELATED APPLICATIONS

This application claims priority to App. Ser. No. 61/894,210, entitled "Bilateral Nasal Cannula", filed Oct. 22, 2013, and to App. Ser. No. 61/931,148, entitled "Bilateral Pure Aroma Human Olfactory Testing Device and Method", filed Jan. 24, 2014, the entire contents of each of which are hereby incorporated by reference.

FIELD OF THE INVENTION

The present invention generally relates to devices, systems and methods for determining relative bilateral olfactory detection thresholds. More specifically, the present invention relates to devices, systems and methods for detecting an asymmetrical differential in a patient's olfactory detection threshold as measured at the left and right nostrils and that, when present, may be used as a device to detect olfactory deterioration resulting from certain neurodegenerative disorders such as Alzheimer's disease.

DESCRIPTION OF THE RELATED ART

Aroma testing in the past has been generally related to the overall aroma detection of a person, commonly by naming a particular odor, without particular interest in comparing the relative smelling ability of their nostrils. Published articles document that a relatively poor sense of smell in the left nostril, or sensitivity, as compared to the sensitivity of the right nostril may be indicative of early brain damage due to neurological disease. See, e.g., Murphy, et al., "Left hippocampal volume loss in Alzheimer's disease is reflected in performance on odor identification: A structural MRI Study", Journal of the International Neuropsychological Society, Vol. 9, No. 3, pp 459-471 (2003). This is the case in Alzheimer's Disease (hereinafter AD), but is of clinical significance in the early detection of AD, however, only if the aroma used in the test is a pure aroma for reasons that are discussed further infra.

It is estimated that up to 40% of the elderly have undiagnosed early on-set Alzheimer's disease, but have not been diagnosed as their dementia is quite mild at this point. Under these circumstances, an early diagnostic tool, e.g., before clinically detectable dementia is observed or diagnosed, is critical to enable therapies to be initiated to slow, or perhaps even reverse, the progression of the disease.

A notable deficit of smelling ability in the left nostril as compared to the smelling ability of the right nostril to detect a pure aroma, appears according to previous medical research, to be indicative of early neurological degeneration of the olfactory nerve, specifically as seen in the early onset of AD.

The olfactory nerve is found on the left side of the brain and is not reversed bilaterally as many brain functions are, such as eye sight. Research, including data from autopsies, indicates that degeneration of the olfactory nerve occurs gradually and begins very early in the disease development of AD. Such deterioration may begin years before substantial dementia becomes notable and, thus currently a diagnosis of AD becomes confirmed by existing testing procedures that are generally focused on observation, detection and/or diagnosis of actual dementia. This technique is, however, problematic in the detection of AD because, inter alia, dementia presents in other non-AD diseases, conditions and/or disorders.

The "pure odorant detection threshold" is the point at which an increasing concentration of pure odorant molecules saturate the olfactory sensory organ to the extent that a cognitive reaction first takes place, where the patient recognizes they are smelling something. There is a latent period between introduction of the pure odorant molecules into the patient's nostrils and when the pure odorant detection threshold is reached. Measurement of this latent period can be of clinical utility. In the case of early onset AD, the latency in the left nostril may be greater than that of the right nostril, providing very early clinical indication of the presence of AD. The olfactory function differential favoring the right side disappears in well advanced AD, as the entire brain deteriorates the right side catches up in deterioration so that both sides are profoundly impacted.

A general process for measuring the left nostril latent period is recently described in the "peanut butter aroma test" reported by Jennifer Stamps at the University of Florida. The Stamps method uses a simple but effective protocol where a common centimeter ruler is held up to the nose of the test subject. The subject is instructed to close their eyes and cover one nostril as a spoonful of peanut butter is slowly moved towards their nose. The clinical technician notes the estimated distance in centimeters between the aroma source and the nostril of the test subject at the point the first aroma detection threshold is noted by the subject. Two testing events might result in the following exemplary pure odorant olfactory threshold values: 12 centimeters on the left nostril and 21 centimeters on the right nostril.

Both the left and right nostrils were tested several times under the Stamps methodology and in random order with a 90-second "reset period" between trials to clear the olfactory gland of the odorant. The relative smelling ability of the two nostrils were then compared using known statistical techniques. Stamps proposes a preliminary standard variation distance of 10 centimeters closer on the left side than the right nostril to be clinically significant as a positive test result. An equal distance measured or a stronger smelling ability on the left as compared to the right nostril, or the left side being only slightly weaker was considered a negative test result. Those with a slight deficiency on the left, i.e., a differential that is less than the selected 10 centimeters variation distance, might still be an indication or warning of early onset of AD.

The estimated clinical result of 95% efficacy using the Stamps method may be improved with a better testing apparatus and a more refined protocol. It was also noted that 100% of those who had already been diagnosed with mild AD by other means had at least the 10 centimeter relative deficiency in the left nostril.

The Stamps methodology uses peanut butter aroma, a pure odorant as that term is defined herein. The capacity to specifically smell "pure odorants", is associated only with stimulating the first cranial nerve. Examples of pure odorants include exemplary compounds such as peanut butter, coffee, vanilla, cinnamon, lavender, almond (bitter), anise, apple, clove, juniper berry, lilac, lemon, orange, pine needle, tar and violet, but include any molecule or compound that only triggers or excites the olfactory nerve and the first cranial nerve but do not also trigger or excite the trigeminal nerve or the 5th cranial nerve. See, e.g., the Scandinavian Odor Identification Test.

Because the use of a "pure odorant" for aroma testing is critical in the context of, inter alia, detection of AD, contamination of the pure odorant with any additional additives or ingredients that might also excite the trigeminal system should be avoided. In addition, common commercial aroma "essential oil" bases and preservatives might tend to coat the airways of the aroma chamber and gas pathways with commercial aroma base oil materials, creating an aroma latency failure mode even where the clear air may be slightly contaminated with aroma. Thus, pure aroma materials used in the test are better diluted with water or trace amounts of alcohol which would evaporate and not leave a latent odor on the interior surfaces of the testing device. Additionally, the lowest concentration and amount of aroma that is still detectable by the user will reduce aroma latency on the air pathways of the device. Certain coatings on the inner surfaces of the devices disclosed herein may also tend to repel the aroma molecules instead of presenting a surface to which the aroma molecules adhere. Alternatively, lining the interior of the aroma presentation device with an electrostatic mat might capture and hold aroma molecules to maintain a clear air pathway without contamination of the pure air. Such mat material can be washed off to recharge the electrostatic resins use in such products as furnace air filters.

The Stamps method comprises some obvious issues rendering it generally unacceptable for repeatable and robust clinical results. Namely, Stamps fails to consider patients' nasal structural issues which may contribute to low airflow and may contribute to poor threshold detection ability in a given nostril. In addition, Stamps fails to consider the general airflow within the testing environment and how that may impact the test results. It is clear that commercialization of the methodology requires a well-defined clinical protocol and more accurate and robust devices and testing methods.

Nonetheless, the Stamps test and other related previously published research papers support the conclusion that an inability to detect a pure aroma relatively equally in both nostrils, especially when the deficit is more notable in the left nostril, may indicate olfactory nerve damage and, therefore, indirectly the early onset of AD.

In addition to the above asymmetrical olfactory threshold discussion, certain disorders or conditions may result in a symmetric olfactory threshold deterioration which may be used to monitor the progression of the underlying disorder or condition and/or the efficacy of a treatment plan designed for the disorder or condition.

A partial listing of conditions or disorders that comprise olfactory dysfunction that may result in either symmetric or asymmetric olfactory threshold deterioration and, therefore, amenable to detection, evaluation and/or monitoring using embodiments of the present invention discussed herein, follows:

Endocrine Conditions or Disorders
Adrenal cortical insufficiency;
Cushing's syndrome;
Diabetes mellitus;
Hypothroidism;
Kallman's syndrome;
Primary amenorrhea;
Pseudohypoparathyroidism; and
Turner's syndrome.
  Neurodegenerative and/or Central Nervous System Conditions or Diseases
Alzheimer's disease;
Parkinson's disease;
Huntington's disease;
Mild cognitive impairment;
Dementia;
Multiple sclerosis;
Epilepsy;
Traumatic brain injury (TBI);
Concussion; and
Intracranial surgery.
  Nutritional Conditions and/or Disorders
Vitamin B12 deficiency (cyanocobalamin);
Renal failure; and
Korsakoff s psychosis.
  Psychiatric Conditions and/or Disorders
Depression;
Olfactory reference syndrome;
Seasonal affective disorder; and
Schizophrenia.
  Local Diseases and/or Mechanical Obstruction of Airway
Adenoid hypertrophy;
Allergic rhinitis;
Atrophic rhinitis (ozena);
Bronchial asthma;
Exposure to toxic chemicals;
Leprosy;
Malignant of paranasal sinuses;
Nasal polyposis;
Sinusitis;
Sjogren's syndrome; and
Vasomotor rhinitis.
  Intranasal Tumors
Frontal lobe glioma;
Hydrocephalus;
Internal carotid aneurysms;
Neuroblastoma;
Suprasellar meningioma;
Sphenoidal ridge meningioma;
Meningioma; and
Aneurisms of the anterior communicating bifurcation.
  Viral and Infections Conditions and/or Disorders
Acute viral hepatitis;
Herpes simplex; and
Influenza.

Thus, a need exists in the art generally for an inexpensive, easy to use, accurate and repeatable clinically significant device, system and method for detecting an asymmetric (left vs right) differential in the olfactory detection threshold of a patient. Such devices, systems and methods may be used to assist a physician in detecting AD and/or risk of developing AD, before the clinical presentation of dementia occurs.

In addition, a need exists for an inexpensive, easy to use, accurate and repeatable clinically significant device, system and method for detecting a symmetric (left vs right) differential in the olfactory detection threshold of a patient.

The present invention addresses these, among other, needs.

BRIEF SUMMARY OF THE INVENTION

The present system is directed in various embodiments to devices, systems and methods for detection, evaluation and/or monitoring olfactory dysfunction by measuring and determining the patient's olfactory detection threshold for the left and the right nostril. More specifically, the present invention relates to devices, systems and methods for detecting an asymmetric differential in a patient's olfactory detection threshold (left vs right nostril) which, when present, may be used as a device to detect, diagnose and/or monitor relative olfactory deterioration resulting from certain neurodegenerative disorders such as Alzheimer's disease.

BRIEF DESCRIPTION OF THE DRAWINGS

FIG. 9 illustrates a cutaway view of one embodiment of the present invention.

FIG. 10 illustrates a cutaway view of one embodiment of the present invention.

FIG. 11 illustrates cutaway view of one embodiment of the present invention.

FIG. 17 illustrates a front side view of one embodiment of the present invention.

FIG. 18 illustrates a side cutaway view of one embodiment of the present invention.

FIG. 19 illustrates a front cutaway view of one embodiment of the present invention.

FIG. 21 illustrates a cutaway view of one embodiment of the present invention.

FIG. 22 illustrates a cutaway view of one embodiment of the present invention.

FIG. 23 illustrates a cutaway view of one embodiment of the present invention.

FIG. 23 illustrates a cutaway view of one embodiment of the present invention.

FIG. 26B illustrates a sectional view of one embodiment of the present invention.

FIG. 31 illustrates one embodiment of a data recordation database for use with the present invention.

DETAILED DESCRIPTION

Figure 1:
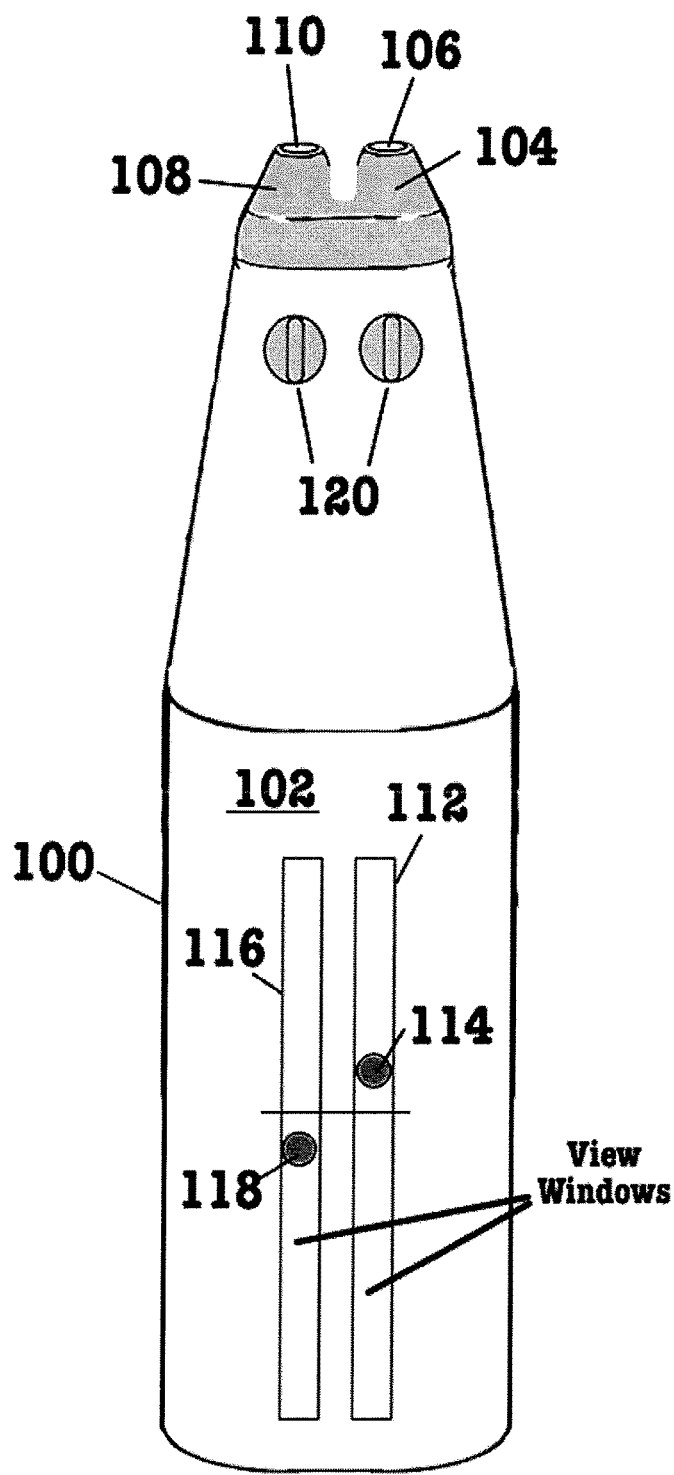
FIG. 1 illustrates a front view of one embodiment of the present invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

The present system is directed in various embodiments to devices, systems and methods for detection, evaluation and/or monitoring olfactory dysfunction by measuring and determining the patient's olfactory detection threshold for the left and the right nostril. More specifically, the present invention relates to devices, systems and methods for detecting an asymmetric differential in a patient's relative olfactory detection threshold (left vs right nostril) which, when present, may be used as a device to detect, diagnose and/or monitor olfactory deterioration resulting from certain neurodegenerative disorders such as Alzheimer's disease.

Definitions

As used herein, "symmetric" or "symmetrical" means that there is not a significant differential in the subject patient's ability to detect and/or identify odors between odors administered and/or inhaled into the patient's left nostril vs. the patient's right nostril as measured by the olfactory threshold determined for each nostril.

As used herein, "asymmetric" or "asymmetrical" means that there is a significant asymmetry or differential in the subject patient's ability to detect and/or identify odors between odors administered and/or inhaled into the patient's left nostril vs. the patient's right nostril as measured by the olfactory threshold determined for each nostril.

"Hyperosmia" is defined as increased olfactory acuity, or a decreased threshold for detecting odors, and may be symmetric or asymmetric as those terms are defined herein. Various embodiments of the present invention may detect and/or monitor hyperosmia or treatments therefore.

"Hypoosmia is defined as diminished or decreased olfactory acuity, or an increased threshold for detecting odors, and may be symmetric or asymmetric as those terms are defined herein. Various embodiments of the present invention may detect and/or monitor hypoosmia or treatments therefore.

"Anosmia" is defined as the inability to recognize odors and may be symmetric or asymmetric as those terms are defined herein. Various embodiments of the present invention may detect and/or monitor anosmia or treatments therefore.

"Dysosmia" is defined as the abnormal sense of smell and may be symmetric or asymmetric as those terms are defined herein. Various embodiments of the present invention may detect and/or monitor dysosmia or treatments therefore.

"Olfactory dysfunction" is defined herein as a patient with a disorder and/or condition with one or more of the following: hyperosmia, hypoosmia, anosmia, and dysosmia. The olfactory dysfunction may be symmetric or asymmetric as those terms are defined herein.

"Pure odorant", also referred to equivalently as "pure aroma" is defined as substances including molecules and/or compounds which principally stimulate the olfactory cell receptors associated with the first cranial nerve and that do not trigger or excite the trigeminal nerve associated with the fifth cranial nerve. A non-exhaustive listing of pure odorants includes peanut butter, coffee, vanilla, cinnamon, lavender, almond (bitter), anise, apple, clove, juniper berry, lilac, lemon, orange, pine needle, tar and violet.

"Odorant" is defined as substances that have a detectable scent and that may stimulate the $1^{st}$ cranial nerve and/or the $5^{th}$ cranial nerve. As a result, "odorant" comprises "pure odorants" as that term is defined herein, as well as other non-pure odorants.

"Pure odorant olfactory threshold" is defined as the point at which the concentration of pure odorant molecules saturate the olfactory sensory organ to the extent that a cognitive reaction first takes place. At this point, the subject patient is able to express that he or she is smelling something. The pure odorant olfactory threshold may be found to be asymmetrical, i.e., significantly different as between the nostrils, indicating olfactory dysfunction. Alternatively, the pure odorant olfactory threshold may be found to be symmetrical between the tested nostrils.

"Odorant olfactory threshold" is defined as the point at which the concentration of aroma molecules saturate the olfactory sensory organ to the extent that a cognitive reaction first takes place. At this point, the subject patient is able to express that he or she is smelling something. The subject patient may not, at this point, be able to immediately identify the aroma by name; a function that is not required for the purposes of the testing methods disclosed herein. The odorant olfactory threshold may be found to be asymmetrical between the nostrils. Alternatively, the odorant olfactory threshold may be found to be symmetrical between the tested nostrils.

"Effective amount" of the pure odorant, or odorant, is defined as the amount of pure odorant, or odorant, required to infuse the aroma airway passage during operation of the various devices, systems and methods of the present invention sufficiently to enable a patient to smell the pure odorant, or odorant, i.e., when saturation of the olfactory sensory organ is sufficient to enable the cognitive reaction of the sense of smell in the patient.

"Clear air", also referred to as pure air, is defined as air that does not comprise the odorant used in the inventive embodiments of the present invention. Preferably, clear air comprises air that is substantially uncontaminated by any odorant, including pure odorants. Clear air may comprise ambient air, i.e., atmospheric air, either filtered or unfiltered, or air that is provided from a clear air source such as an air tank or nebulizer and/or from a mechanized powered air pump as is well known in the art.

Figure 2:
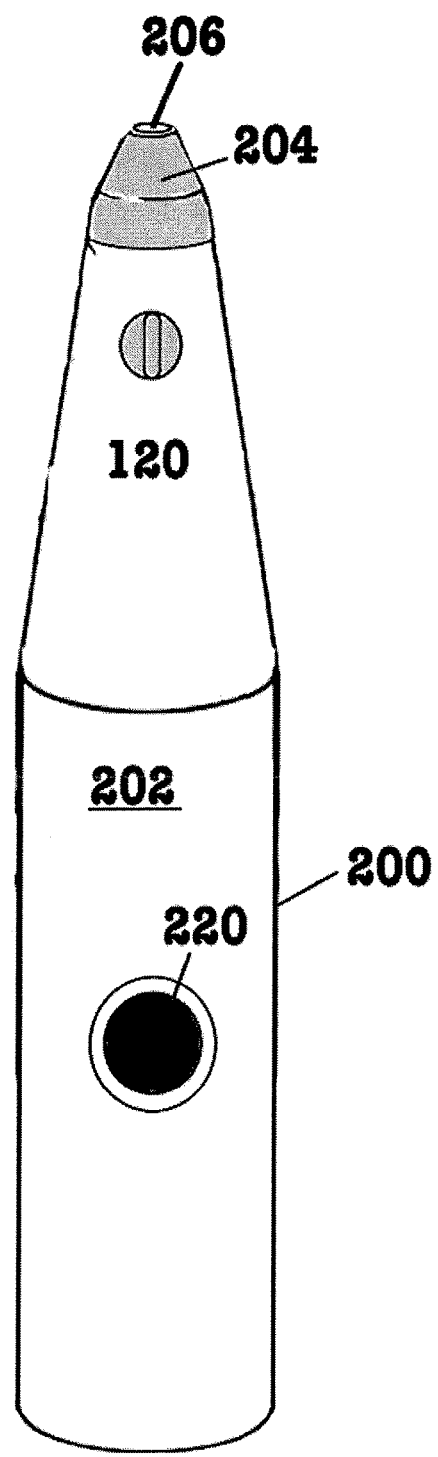
FIG. 2 illustrates a front view of one embodiment of the present invention.

Turning now to the Figures, FIG. 1 illustrates a front side view of a two-nasal tip device embodiment 100 of the present invention while FIG. 2 illustrates a front side view of a single nasal tip embodiment 200 of the present invention. FIG. 1 thus comprises a housing 102 having a left nasal tip 104 and a right nasal tip 108 attached thereto. Left nasal tip 104 comprises a lumen 106 therethrough, while right nasal tip 108 comprises a lumen 110 therethrough. The front side of FIG. 1 further comprises a left airflow meter 112 with a floating ball 114 that rises and falls to show relative airflow within the left airway passage (shown in later Figures) defined by housing 102 and within which floating ball 114 resides. FIG. 1 also illustrates a right airflow meter 116 that also comprises a floating ball 118 therein and that rises and falls within the right airway passage (also shown in later Figures) defined by housing 102 and within which floating ball 118 resides. Floating balls 114, 118 are visible through viewing windows. FIG. 1 also provides a pair of one-way valves 120 (shown in later Figures) arranged near the nasal tips 104, 108 to allow the patient using the device to exhale.

FIG. 2 shows a front side view of a single nasal tip embodiment 200. The front side of the single nasal tip embodiment 200 may be similar to that of FIG. 1 by comprising an airflow meter with a floating ball, provided to provide relative information about the airflow. FIG. 2 differs from FIG. 1 in that FIG. 2's embodiment comprises a single airway passage defined by housing 202, so only a single nasal tip 204 having a lumen 206 therethrough is required as well as a single airflow meter to monitor the single airway passage airflow, if provided. FIG. 2 also provides a one-way valve 120 (shown in later Figures) arranged near the nasal tip 204 to allow the patient using the device to exhale.

An activation button 220 is illustrated disposed on the side of housing 202 allowing activation of the device 200. The activation button 220 may be electrical or mechanical, but when activated by depressing or actuating the button 220, the device 200 begins delivering odorant-infused air, or clear air, to the lumen 206 of the nasal tip 204 and, from there, into a nostril of the patient in a controllable manner.

The rear side of the device 100 of FIG. 1 may similarly include an activation button as disclosed in FIG. 2 to initiate delivery of odorant-infused air, or clear air, to the lumens 106, 110 of nasal tips 104, 108 in a sequential and controllable manner. Further details on both of the embodiments 100 and 200 and their respective elements will be provided infra.

FIGS. 3A, 3B, 4, 5, 6 and 7 illustrate one system 300 embodiment in use with a patient and comprising a housing 302 having a left nasal tip 304 having a lumen therethrough (not shown) and a right nasal tip 306 with a lumen therethrough (not shown) and an air inlet 307. System 300 also comprises a nasal cannula 310 with a left air supply line 312 attached to the left nasal tip 304 by a connector 308 and a right air supply line 314 attached to the right nasal tip 306 by a connector 308, each air supply line 312, 314 comprise a lumen to permit air flow therethrough as is commonly understood. Nasal cannula 310 is similar to the typical oxygen delivery device widely used in the medical industry. In certain embodiments, the air supply lines 312, 314 may comprise a diameter that is slightly wider than those in the typical oxygen delivery device in order to aid in allowing aroma-infused air, or clear air, to flow freely enough to trigger the patient's pure odorant, or odorant, threshold and without depriving the patient of a sufficient air supply. There is a blocking element 316 between the left cannula airflow outlet 318 and the right cannula airflow outlet 320, effectively dividing the cannula 310 into two separate cannula pathways for the left and the right nostrils, respectively, allowing for isolation air flow to each nostril when desired.

System 300 further comprises a mechanical powered clear air source 322 that may be powered by a battery or electricity, e.g., a nebulizer or powered air pump. Clear air source 322 comprises a clear air outlet (not shown but as is commonly known by the skilled artisan) to which is attached an air hose 324 which, in turn, is connected to the air inlet 307 of housing 302, air inlet 307 having a lumen 309 therethrough. Clear air is pumped or otherwise provided to air inlet 307 and lumen 309 which allows fluid communication of the clear air into a clear air compartment 311.

Housing 302 further comprises a switching mechanism 350, best illustrated by reference to FIGS. 4 and 5, which allows a user to switch between (1) providing odorant infused air to the patient's left nostril while providing clear air to the right nostril, wherein switching indicator 352 may indicate "L" or "Left", (2) providing odorant infused air to the right nostril while providing clear air to the left nostril, wherein switching indicator 352 may indicate "R" or "Right" and (3) providing clear air to both the left and right nostrils, wherein switching indicator 352 may indicate "C" or "Clear".

Figure 3A:
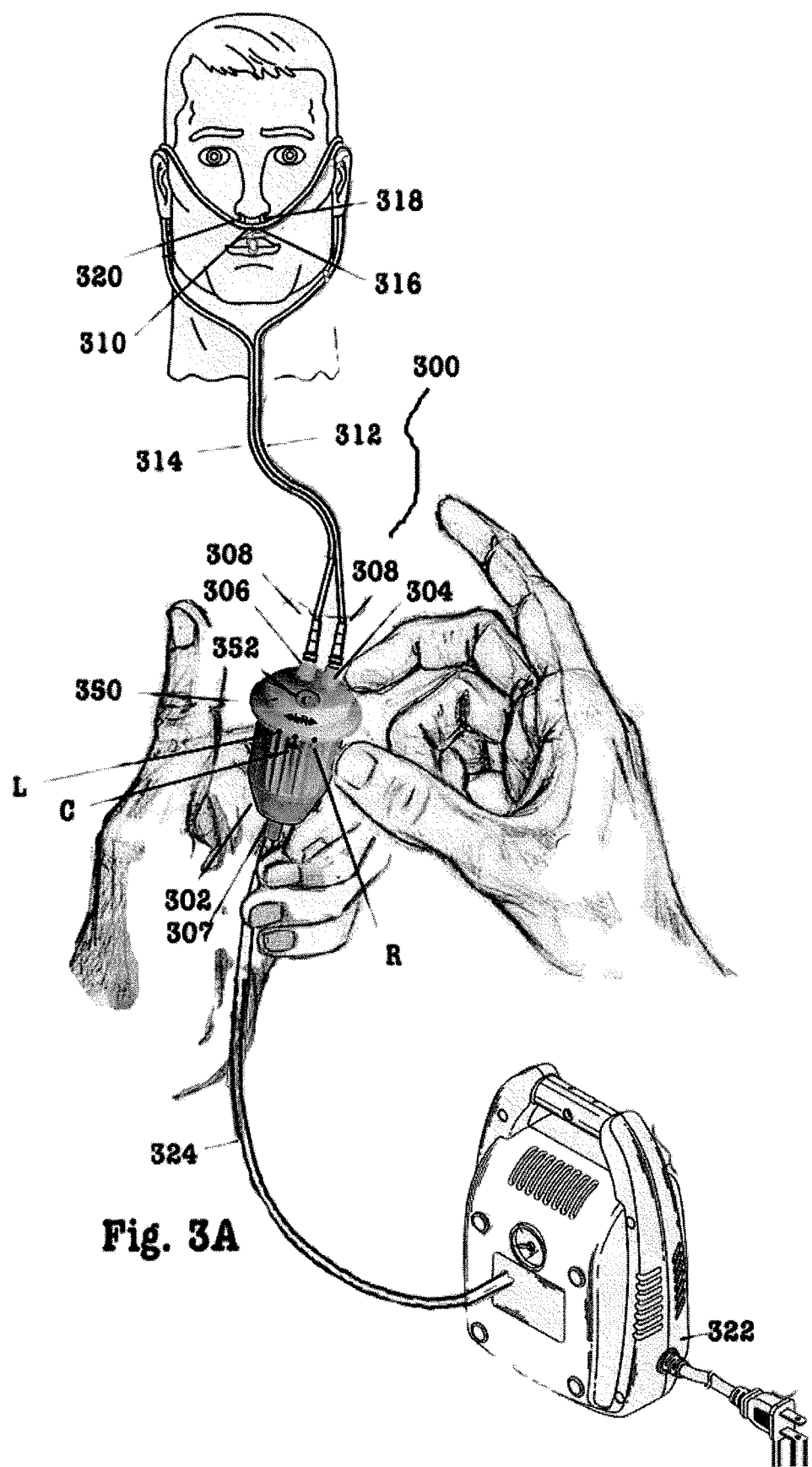
FIG. 3A illustrates one embodiment of the present invention.
Figure 3B:
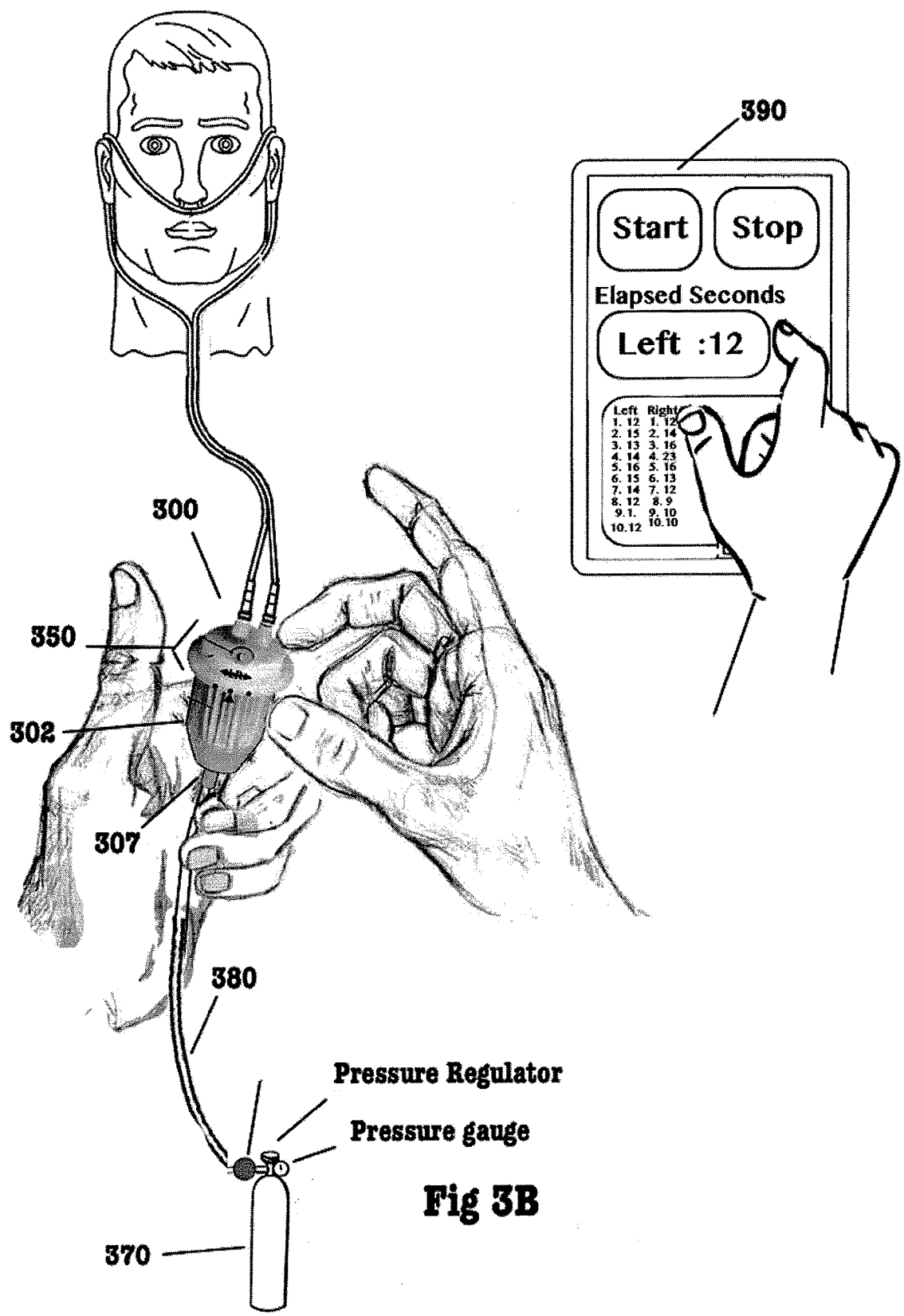
FIG. 3B illustrates one embodiment of the present invention.

FIG. 3B illustrates an alternative system to that of FIG. 3A in that a pressurized canister of breathable clear air 370 is provided with a pressure regulator and gauge. Clear air supply line 380 connects with the pressurized canister 370 for transporting clear air under pressure to clear air inlet 307 of housing 302. Switching of the device 300 is accomplished in the same manner as that of FIG. 3A as is the delivery of clear air and odorant, or pure odorant, infused air to each nostril. The remainder of the system of 3B is the same as disclosed for FIG. 3A. Computerized appliance 390 is also provided as in the system of FIG. 3A.

Figure 4:
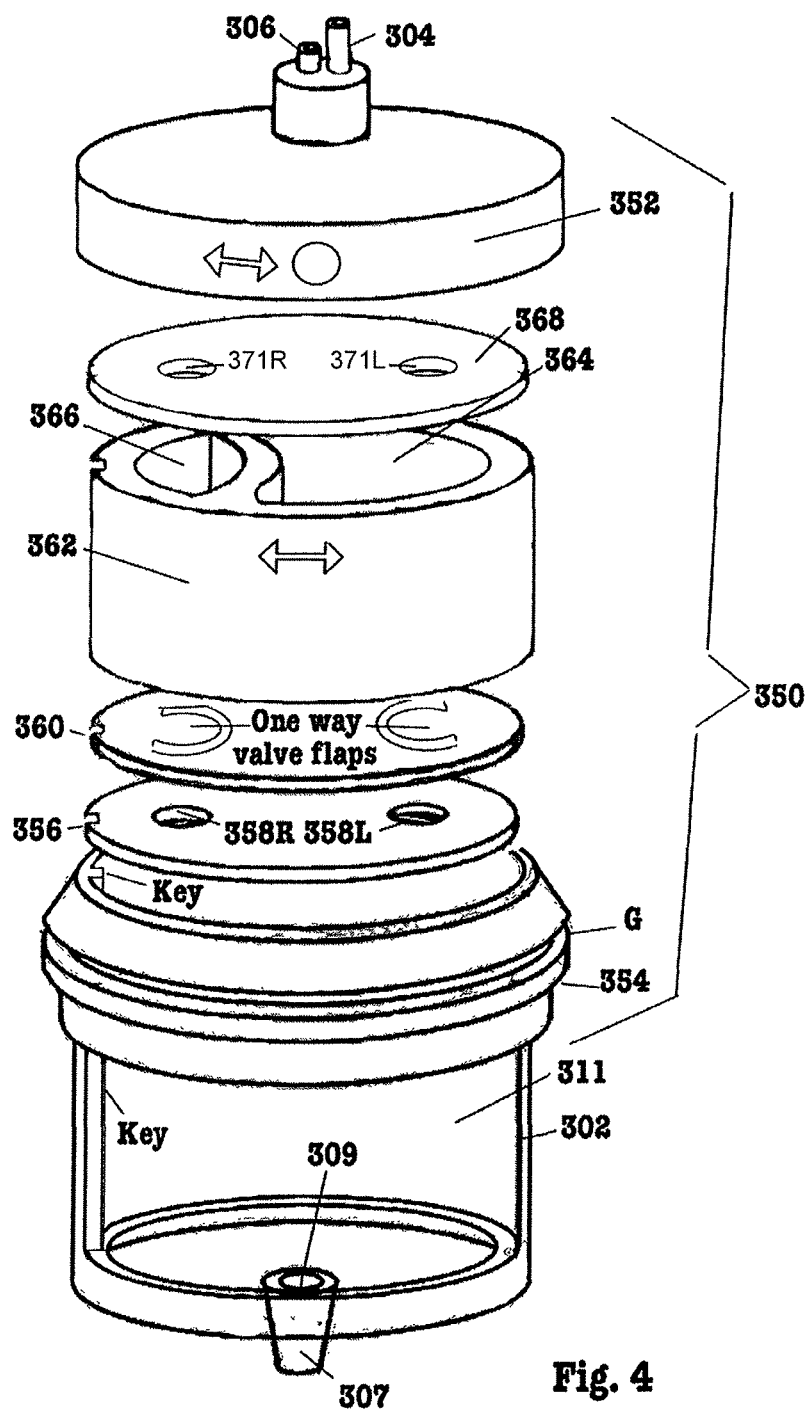
FIG. 4 illustrates an exploded view of one embodiment of the present invention.

FIG. 4 illustrates an exploded view of actuating switching mechanism 350 and its relationship to housing 302. Switching mechanism 350 comprises a cap 352 which also supports left and right nasal tips 304, 306 and which rotationally engages groove G on cap attachment 354 which is fixedly attached to housing 302 as illustrated. Cap attachment 354 does not have a top covering surface, instead, lower disk 356, with two clear air ports 358 therethrough and in communication with clear air compartment 311 of housing 302, is disposed on the top rim of cap attachment 354. Next, rubber flap disk 360 comprising one way valves is disposed on the top surface of lower disk 356, each one way valve in alignment and one-way fluid communication with clear air chamber 311 and allowing air flow from clear air chamber 311. Rotating barrel 362 is disposed on the top surface of rubber flap disk 360 and comprises an odorant, or pure odorant, compartment 364 where the odorant, or pure odorant, source resides, and a clear air passage 366 therethrough and in communication with at least one of the right and left clear air ports 358R, 358L at all times and in all switching indications, i.e., Left, Right or Clear. Cap washer 368 is disposed on the top surface of barrel 362 and comprises a right and left air ports 371R, 371L therethrough. Rotating barrel 362 is rotatable relative to the cap 352 to three basic positions: Left (where odorant infused air is presented to the left nostril, but not the right); Right (where odorant infused air is presented to the right nostril, but not the left); and Center (where clear air is presented to the right and the left nostril).

In the Left position, rotating barrel 362 is rotated relative to cap 352 so that clear air flows out of clear air chamber 311, through the left clear air port 358L and its associated one-way valve and into the odorant compartment 364 where the air is infused with molecules of odorant, or pure odorant, residing in compartment 364. At the same time, additional clear air flows out of clear air chamber 311, through the right clear air port 358R and its associated one-way valve and into the clear air compartment 366. The infused air flows out of compartment 364, through left air port 371L and into the lumen of the left nasal tip 304 for presentation to the patient's left nostril and airway. The flow of infused air from clear air chamber 311 to the patient's nostril as described is an aroma airway passage. The clear air flows out of clear air compartment 366 through right air port 371R and into the lumen of right nasal tip 306 for presentation to the patient's right nostril. The flow of clear air from clear air chamber 311 to the patient's nostril as described is the clear airway passage. This position is used to detect the patient's left airway passage odorant, or pure odorant, threshold while clearing the right airway passage of any residual odorant, or pure odorant.

In the Right position, rotating barrel 362 is rotated relative to cap 352 so that clear air flows out of clear air chamber 311, through the right clear air port 358R and its associated one-way valve and into the odorant compartment 364 where the air is infused with molecules of odorant, or pure odorant, residing in compartment 364. At the same time, additional clear air flows out of clear air chamber 311, through the left clear air port 358L and its associated one-way valve and into the clear air compartment 366. The infused air flows out of compartment 364, through right air port 371R and into the lumen of the right nasal 306 tip for presentation to the patient's right nostril and airway. The flow of infused air from clear air chamber 311 to the patient's nostril as described is the aroma airway passage. In contrast, the clear air flows out of clear air compartment 366 through the left air port 371L and into the lumen of left nasal tip 304 for presentation to the patient's left nostril. This flow of clear air from clear air chamber 311 to the patient's nostril as described is the clear airway passage. This position is used to detect the patient's right airway passage odorant, or pure odorant, threshold while clearing the left airway passage of any residual odorant, or pure odorant.

In the Center position, the rotating barrel 362 and cap 352 are positioned relative to each other so that no air flow can move through the odorant, or pure odorant, compartment 364. In this position, the air flow for both the left and right nostril tips 304, 306 moves from clear air chamber 311, through clear air compartment 366 and into the lumen of tips 304, 306 for presentation of clear air only to the patient's right and left nostrils. This position is used to clear both the right and left airways of the patient of any residual odorant, or pure odorant.

Thus, this embodiment of the invention may be used to switch between an aroma infused airway passage to a clear airway passage and from a clear airway passage to an aroma airway passage for an individual nostril.

Figure 5A:
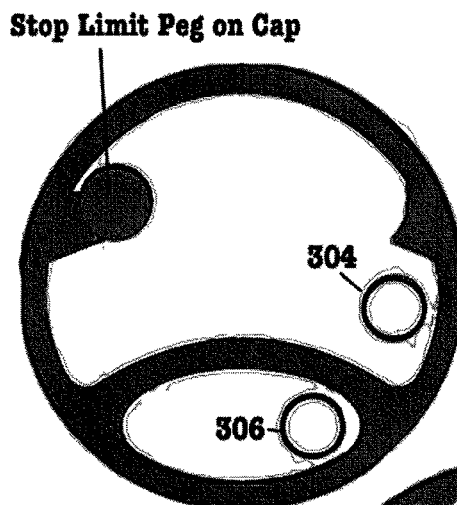
FIG. 5a illustrates a sectional view of one embodiment of the present invention.
Figure 5B:
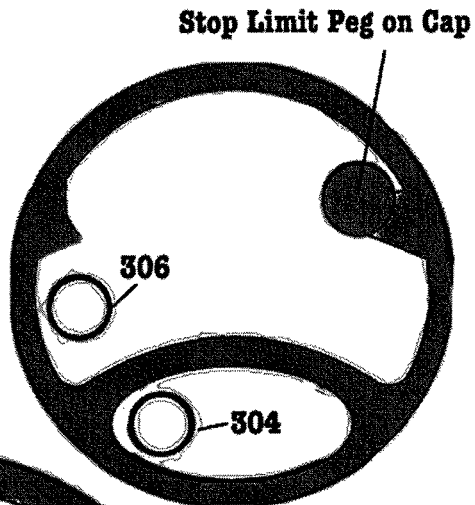
FIG. 5b illustrates a sectional view of one embodiment of the present invention.
Figure 5C:
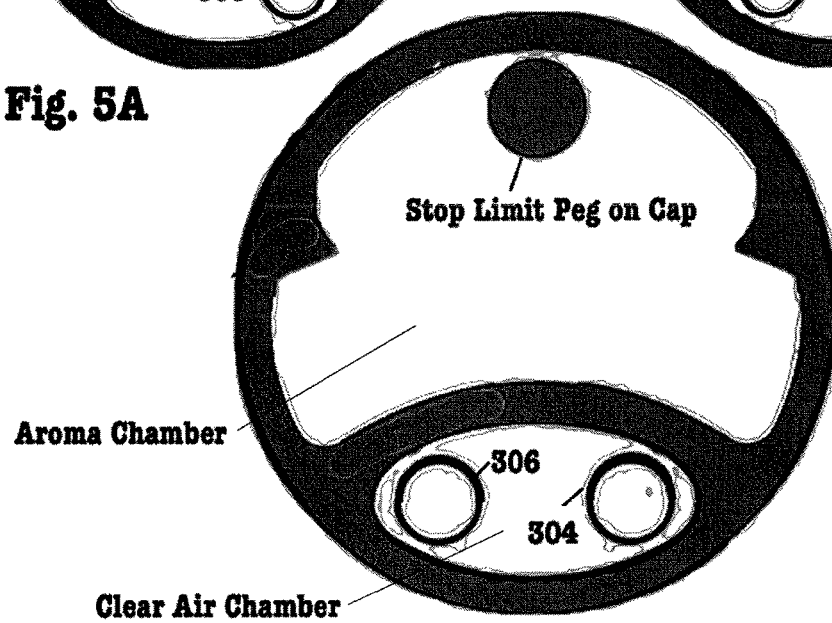
FIG. 5c illustrates a sectional view of one embodiment of the present invention.

Turning now to FIGS. 5A, 5B and 5C, the three possible switching positions for the switching mechanism 350 are illustrated in additional detail. In FIG. 5A, the left nasal tip 304 is illustrated as switched into fluid communication with the aroma airway passage, with odorant, or pure odorant, infused airflow moving into and through the left nasal tip 304. Left nasal tip 304 is also switched out of fluid communication with the clear airway passage. The right nasal tip 306 is, on the other hand, is switched into fluid communication with the clear airway passage and out of fluid communication with the odorant, or pure odorant, infused airway passage. Here, the left nostril of the patient receives airflow infused with the odorant, or pure odorant through the aroma airway passage, while the right nostril of the patient receives a clear airflow through the clear airway passage.

FIG. 5B illustrates the left nasal tip 304 as switched into fluid communication with the clear airway passage and out of communication with the aroma infused airway passage. The right nasal tip 306 is switched into fluid communication with the odorant, or pure odorant, infused airway passage and out of fluid communication with the clear airway passage. In this case, the right nostril of the patient receives airflow infused with the odorant, or pure odorant through the aroma airway passage, while the left nostril of the patient receives a clear airflow through the clear airway passage.

Finally, FIG. 5C illustrates both the left nasal tip 304 and the right nasal tip 306 switched out of fluid communication with the odorant, or pure odorant, infused airway passage and into fluid communication with the clear airway passage. Here, both nostrils of the patient receive clear airflow through the clear airway passage.

The stop limit peg on cap shown in FIGS. 5A, 5B and 5C comprises a mechanism for stopping the rotation of the cap at aroma passage alignment in FIGS. 5A and 5C, but clear air when aligned with the clear air passage.

Figure 6:
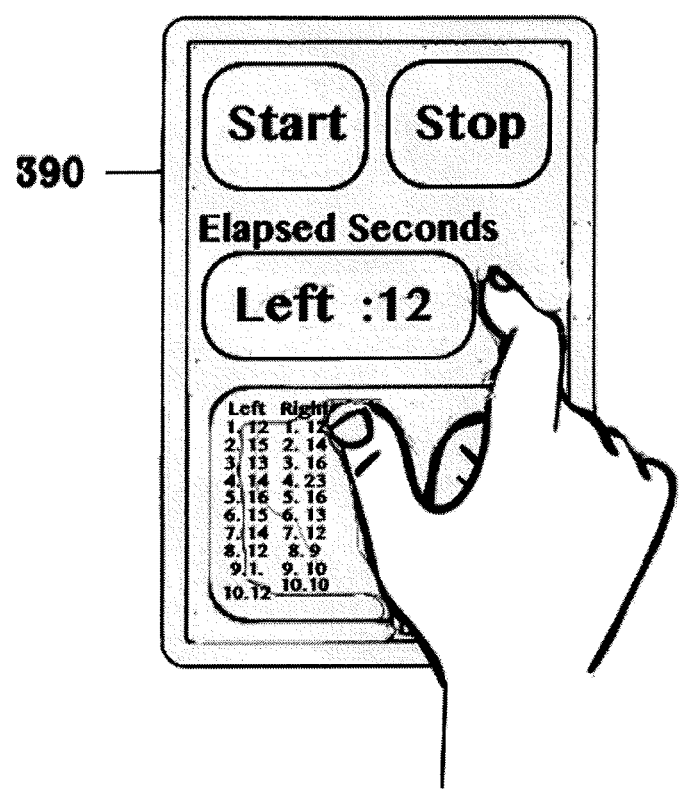
FIG. 6 illustrates one embodiment of the present invention.

Referring now to FIG. 6, system 300 may further comprise a computerized accessory 390 having a display that may have an actuating start button and an actuating stop button as illustrated which starts and stops a timer that captures the duration of the latent period between actuation of the system's aroma airway passage, i.e., when the switching mechanism 350 is switched to either Left or Right, and the time when the patient recognizes an odor. The latency time for each nostril (left and right) to reach the odorant, or pure odorant, threshold and the number of trials, in the illustration ten trials are recorded, may be automatically filled in by the computerized accessory upon actuation of the stop button, or the user may fill in the observed trial data into a preformatted database. When the required number of trials has been completed, the computerized accessory may do a comparison of the captured data using an application or algorithm executing well-known statistical comparative techniques and served by a central server.

In the simplest embodiment, the left nostril trial data is summed, the right nostril trial data is summed, and the two sums are compared for symmetry or asymmetry according to standard statistical means. Most simply and without limitation, if the number of trials is 10, asymmetry may be determined to be present if the summation of one nostril differs from the summation of the other nostril by a total of one or more seconds. Other summation differentials may be employed as the skilled artisan will recognize, each of which are within the scope of the present invention. Alternatively, a more formal statistical analysis may be used to compare the data, the techniques are within the realm of the skilled artisan. What is important is that the trial data be captured and compared for symmetry or the presence of asymmetry.

The data comparison may be done by the operator by hand or, alternatively, the computerized accessory may comprise a memory with executable instructions for comparing the trial data and a processor for executing the executable instructions when the trial data is to be compared.

Figure 7:
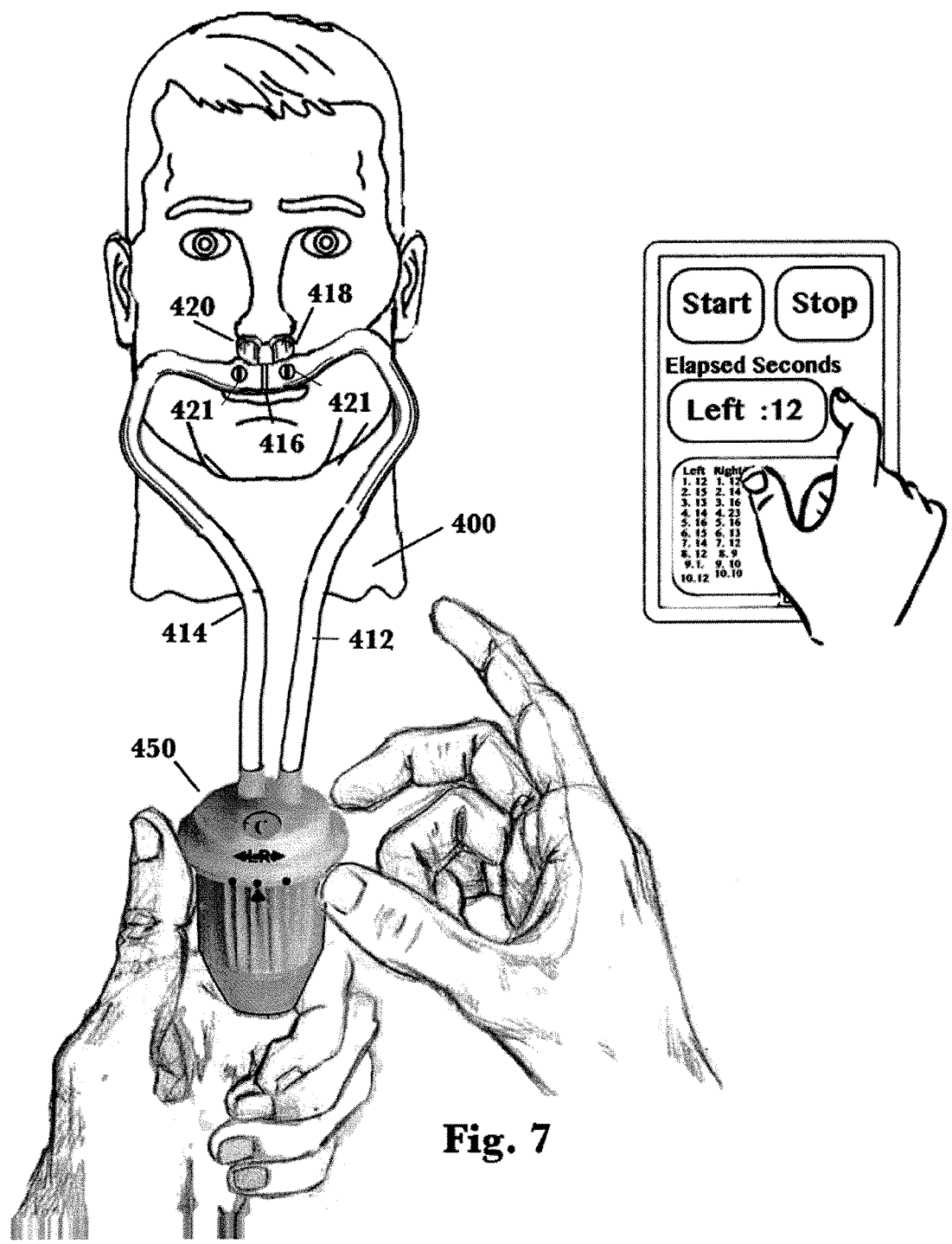
FIG. 7 illustrates embodiment of the present invention.

FIG. 7 illustrates an alternate embodiment 400, similar to that disclosed above regarding system 300, except that in this alternate construction, there is no powered air flow supply to the housing. Instead, the device 400 comprises an air flow that is initiated by the patient's inhalation. This embodiment comprises enlarged lumens, for example and without limitation 9 mm or larger diameter, in the left and right air supply lines 412, 414 as well as enlarged cannula air outlets 418, 420 to ensure a tighter fit to further enable the inhalation-driven air flow through device 400. Blocking element 416 ensures that the left and a right air passages are separated, wherein air flow through the left or right air passage is controllable with switching mechanism 450 that operates in the same manner as that of switching mechanism 350 described supra. Finally, each air supply line 412, 414 comprise a one-way valve 421 disposed proximate to the left and right enlarged cannula air outlets 418, 420 to enable free exhalation during the procedure and to prevent the patient from either exhaling (and potentially inhaling) through the mouth or hyperventilating.

FIGS. 8A-11 illustrate an inhalation powered single nostril device 500 comprising a housing 502, with a soft nasal tip 504 which may be removable and/or disposable, e.g., a commonly known disposable nasal specula tip, an activation switching mechanism 506, with clear air channel 507 therethrough, and a one-way exhalation valve 520. In addition, an odorant, or pure odorant, compartment 521 is defined within the housing, wherein an odorant, or pure odorant, source is located and, as a result, odorant, or pure odorant, infused air is also within compartment 521. As FIG. 9 shows, when a patient exhales downward through the soft nasal tip 504, the exhaled air encounters a clear air one-way valve 522 and is deflected therefrom and out of the device 500 through exhalation valve 520.

When the patient inhales, FIG. 10 illustrates the clear air pathway that results when the activation switching mechanism 506 is not activated or actuated allowing the clear air channel 507 to be aligned with the clear airway passage 550 (illustrated by the arrows), blocking access to the compartment 521 where odorant, or pure odorant, source and infused air is located. Switching mechanism is held in a biased unactivated position by an opposing spring as shown. In this case, upon patient inhalation, clear air enters the device 500 at clear air entry 524 and is drawn up through clear airway passage 550 illustrated by the arrows and defined by housing 502. In this case, the upwardly flowing clear air moves through the one-way valve 522 and into the patient's nostril.

FIG. 11 illustrates the case when the device 500 is activated by activating switching mechanism 506, pushing the switching mechanism 506 inward toward the housing and overcoming the spring's biasing force taking the clear air channel 507 out of alignment with the clear air passage 550, thus the clear air passage is blocked by the actuating switching mechanism 506. In this event, the clear air enters the housing at the clear air entry 525 and passes through the odorant one-way valve 526 and into the odorant, or pure odorant, compartment 521 where odorant source, or pure odorant source, 523 and infused air is located. The clear air becomes infused with odorant, or pure odorant in compartment 521 and travels along the aroma airway passage 560 as illustrated by the arrows, ultimately passing through one-way valve 522 and into the patient's nostril.

Figure 8A:
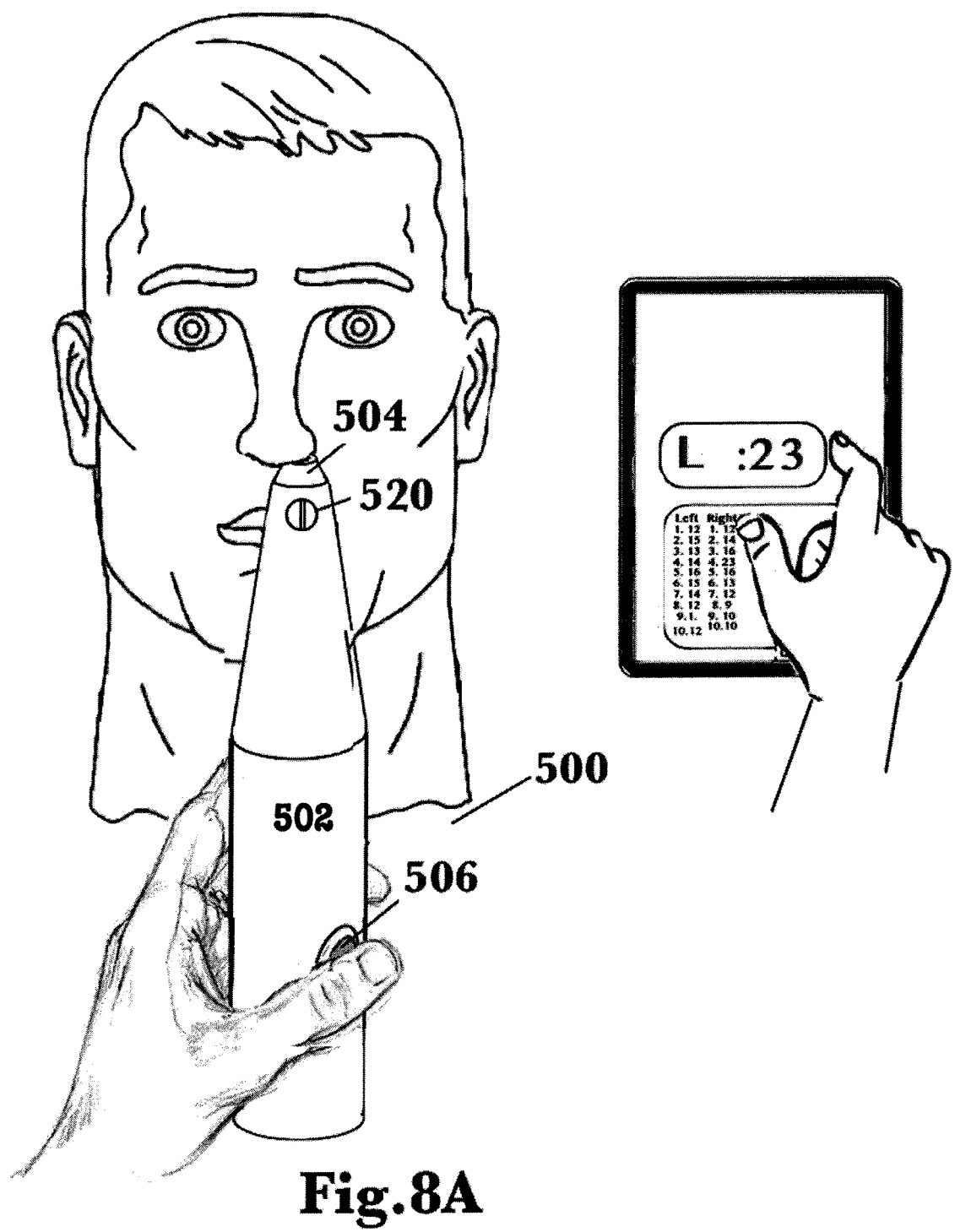
FIG. 8a illustrates one embodiment of the present invention.
Figure 8B:
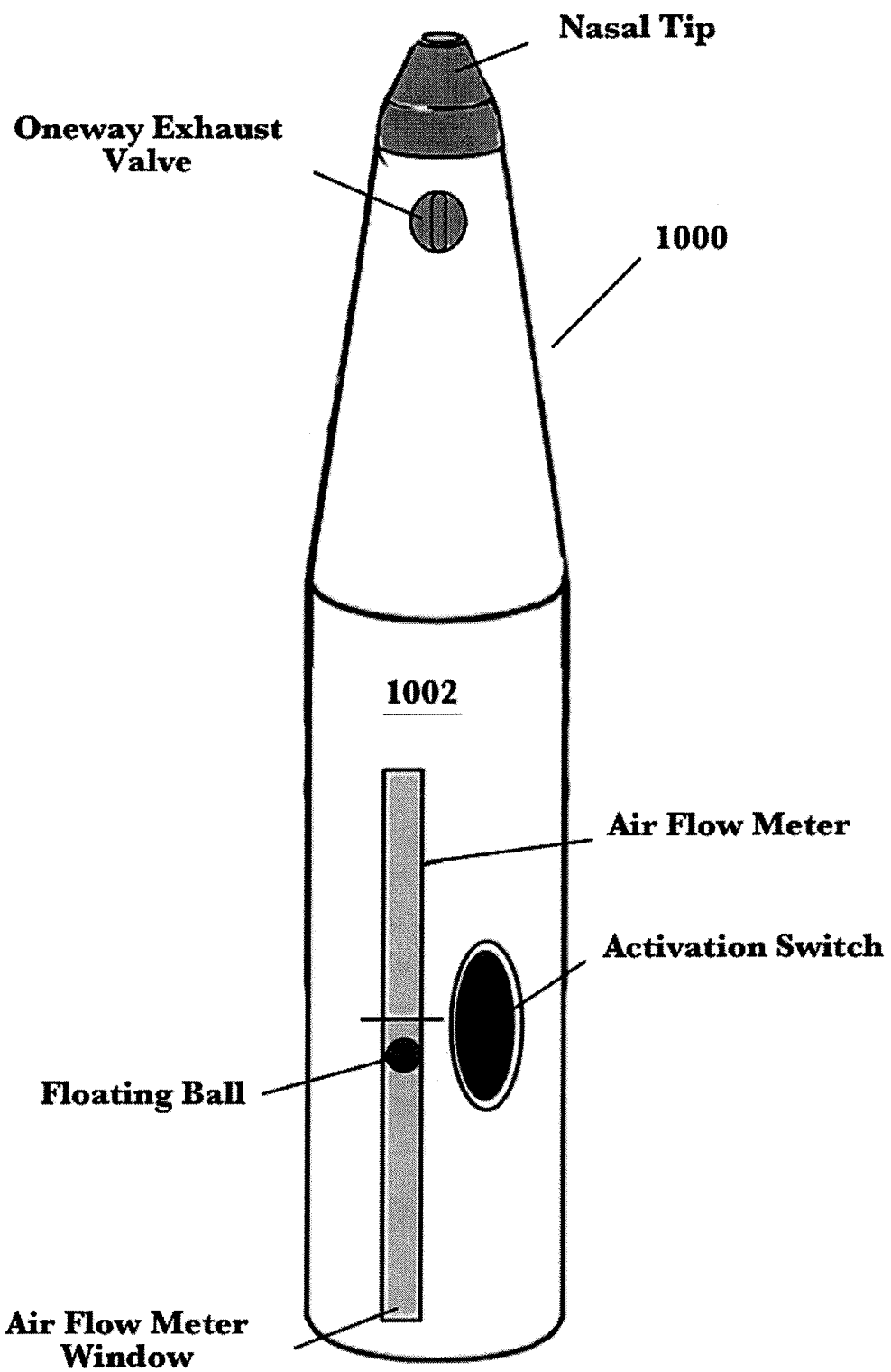
FIG. 8b illustrates one embodiment of the present invention.

FIG. 8B provides a device 1000 similar to device 500 of FIG. 8A except that an airflow meter is provided with a floating ball disposed within airway channel defined by housing 1002 and by airflow meter window. Device 1000 is activated by the patient's inhalation, causing clear air to enter a clear air inlet as in FIG. 18 and through air port 932 as in FIG. 18. The clear air passes through an airflow channel through one-way valve and into the nasal tip and ultimately into the patient's nostril as shown in FIG. 18 thus comprising a clear airway passage. An exhalation one-way valve as shown as element 920 in FIG. 18 is also provided with the same exhalation air passage. Activation of the activation switch results in activation of the odorant, or pure odorant, source like element 932 of FIG. 18 which, when driven by the inhalation force provided by the patient, rises upwardly through the airflow channel, through the one-way valve as in FIG. 18, through the nasal tip and into the patient's nostril, thus comprising an aroma airway passage.

Figure 12:
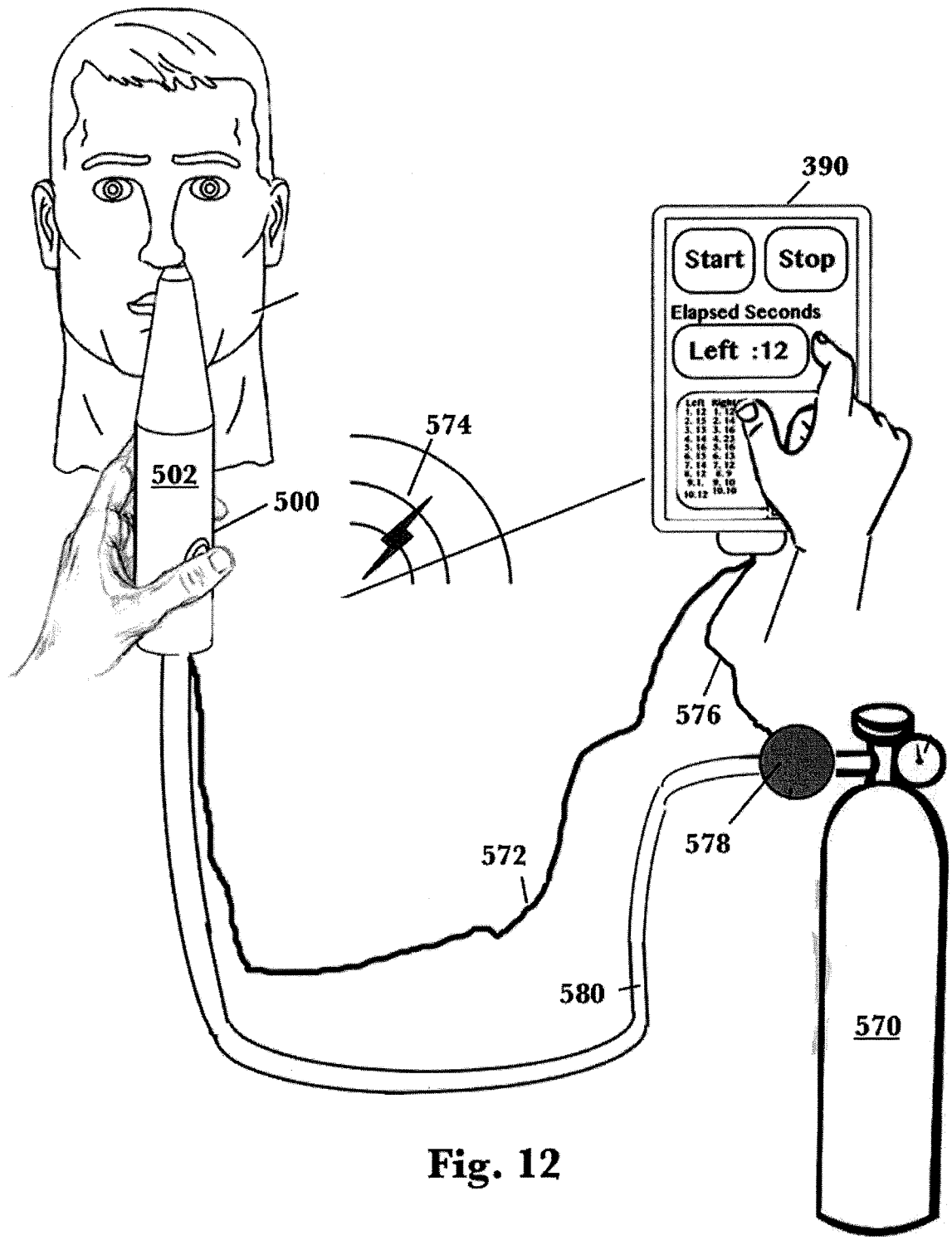
FIG. 12 illustrates one embodiment of the present invention.

FIG. 12 illustrates a device similar to device 500 within a system comprising a pressurized pure air source supply 570 and with a computerized accessory or appliance 390 as previously discussed in connection with FIG. 6. The device 500 is, however, connected to the computerized appliance 390 by hardwire 572 and/or by Bluetooth® connectivity 574 as those connection methods are well known to the skilled artisan. The computerized appliance 390 may also connected 576 with an odorant, or pure odorant, source which is housed within the housing 502 of device 500 in the same manner as described in connection with FIGS. 9-11, where the odorant, or pure odorant, is identified as element 523 and disposed within the odorant, or pure odorant, compartment 521. Pressurized pure air source supply 570 is in fluid communication with air supply regulator 578 and air hose 580 which is also in fluid and switchable communication with odorant, or pure odorant, source 578 and odorant, or pure odorant, inlet 525 as in FIGS. 9-12. In this embodiment, however, the air flow from the pressurized pure air source supply 570 is regulated which, in turn, regulates the odorant, or pure odorant, concentration moving through device 500 when in aroma airway mode and through the aroma airway passage. When switched to clear airway mode by shutting off the pressurized pure air source supply 570, the patient's inhalation initiates clear air flow through the device 500 via clear air inlet 524 as previously described through clear airway passage.

The skilled artisan will readily understand that the system of FIG. 12 as applied to single nasal tip device 500 may also easily be applied to a dual nasal tip device such as device 100 in FIG. 1 and as will be described in more detail infra.

Figure 13:
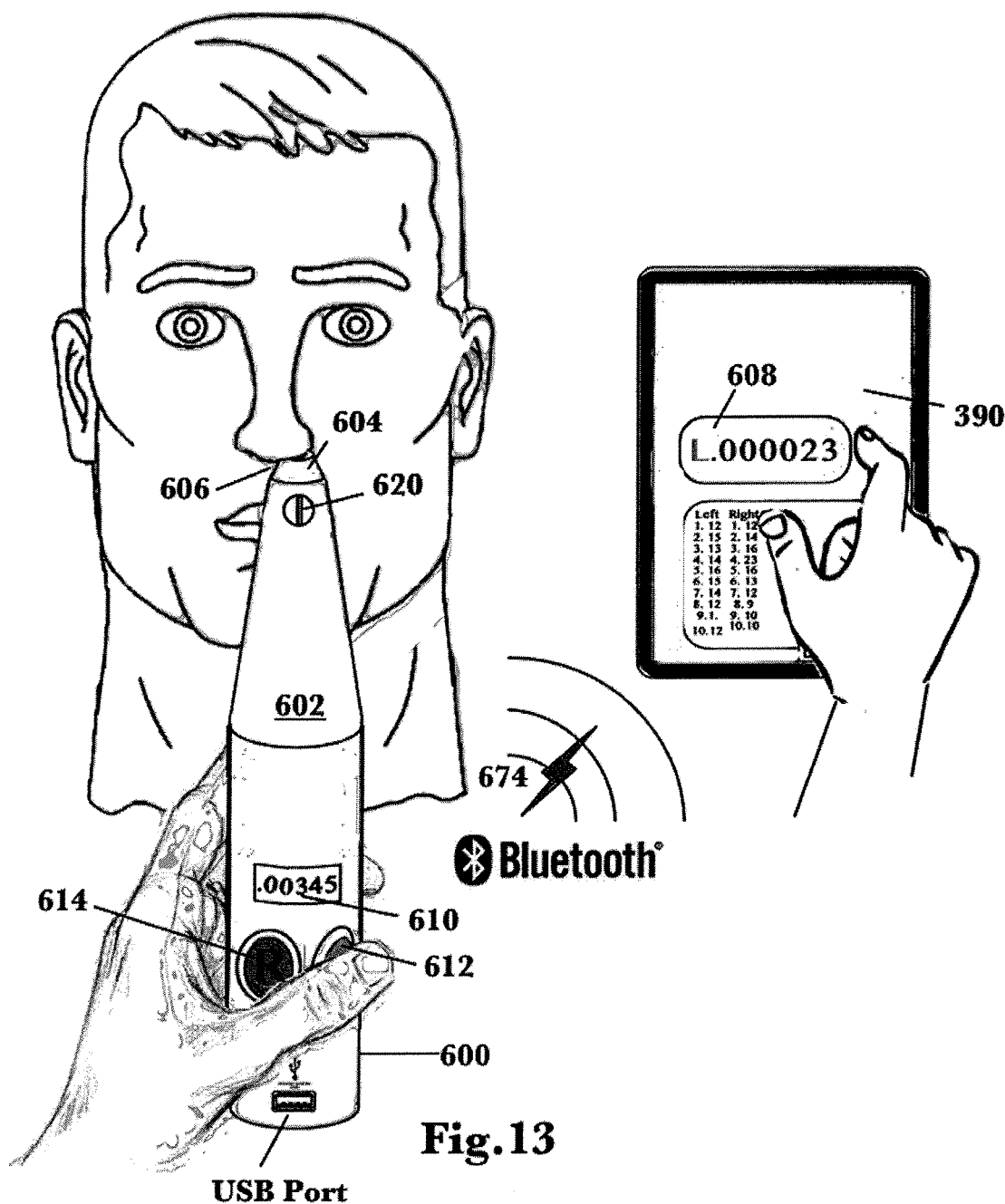
FIG. 13 illustrates one embodiment of the present invention.

FIG. 13 illustrates an embodiment of a system comprising device 600 similar to device 500 and having a single nasal tip 604 and a one-way valve 620 to assist with exhalation along an exhalation airway as previously described. Device 600 differs from device 500 in that it comprises an electronic nose module 606 to detect the concentration of odorant, or pure odorant, proximate the patient's nostril and as is well understood in the art, a nose concentration digital readout 608 on the computerized application 390 that records the concentration of odorant, or pure odorant, at the patient's nostril as well as the time latency for each nostril and each trial. The device 600 is connected to the computerized application 390, as illustrated, by Bluetooth®, however a hard wire connection as in FIG. 12 may also be used. The device 600 also comprises a digital readout 610 of the concentration of the odorant, or pure odorant, within either the odorant, or pure odorant, compartment or at some point within the aroma airway passage as those structures are described in connection with device 500, using a sensor to measure the concentration (not shown but as is well known to the skilled artisan). Further, device 600 also comprises left nostril switch 612 and right nostril switch 614. These switches 612, 614 enable the data for each nostril and for each trial to be sent to the computerized appliance or accessory 390 and captured within a database table and compared as previously discussed when all of the trials have been completed. Note in this connection that, as illustrated, the left nostril switch 612 is activated with the nose concentration measured and displayed on the nose concentration digital readout 608 as "L.000023" indicating that the left nostril has a concentration of 0.000023 units. This data is subsequently recorded in the database for possible analysis.

Figures 14, 15:
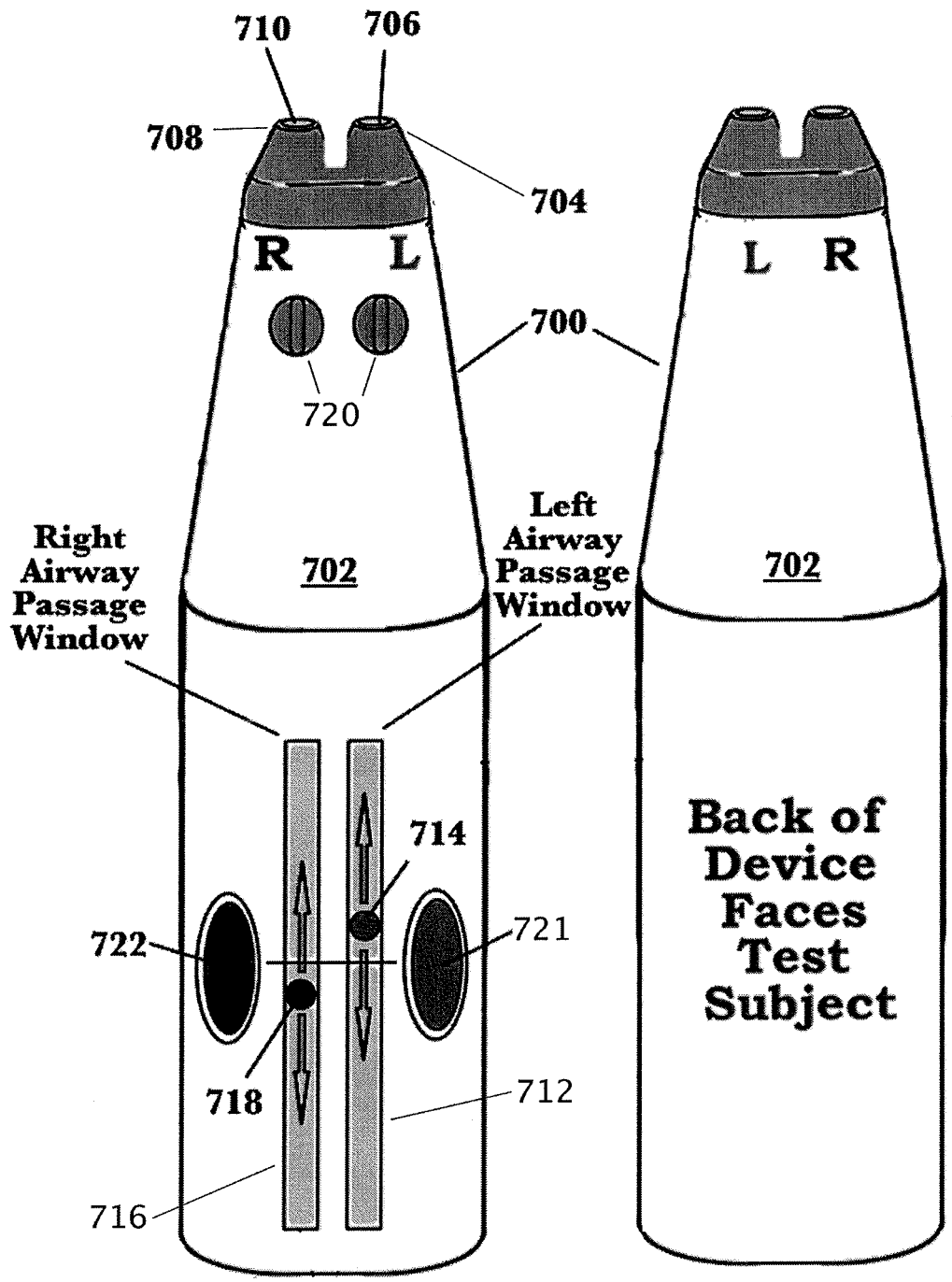
FIG. 14 illustrates a front side view of one embodiment of the present invention.
FIG. 15 illustrates a rear side view of one embodiment of the present invention.

FIGS. 14 and 15 illustrate a two nasal tip device 700 similar to device 100 of FIG. 1. Thus, device 700 comprises a housing 702 having a left nasal tip 704 and a right nasal tip 708 attached thereto. Left nasal tip 704 comprises a lumen 706 therethrough, while right nasal tip 708 comprises a lumen 710 therethrough. FIG. 14 illustrates a front view of device 700 and further comprises a left airflow meter 712 with a floating ball 714 that rises and falls to show relative inhalation, but not exhalation, airflow within the left airway passage defined by housing 702 and described supra and within which floating ball 714 resides. Device 700 further comprises a right airflow meter 716 with a floating ball 718 that also rises and falls within the right airway passage defined by housing 702, described supra, and within which floating ball 718 resides and a pair of one-way valves 720 arranged near the nasal tips 704, 708 to allow the patient using the device to exhale during clear airway mode as previously described. Finally device 700 comprises a left nasal activation switch 721 and right nasal activation switch 722 which, when activated, initiate odorant, or pure odorant, infused air through the aroma airway passage and into the patient's left or right nostril, respectively. FIG. 15 provides a rear side view with an orientation message designed to avoid turning the device the wrong way and obtaining mistakenly reversed data from the nostrils as a result.

Figure 16:
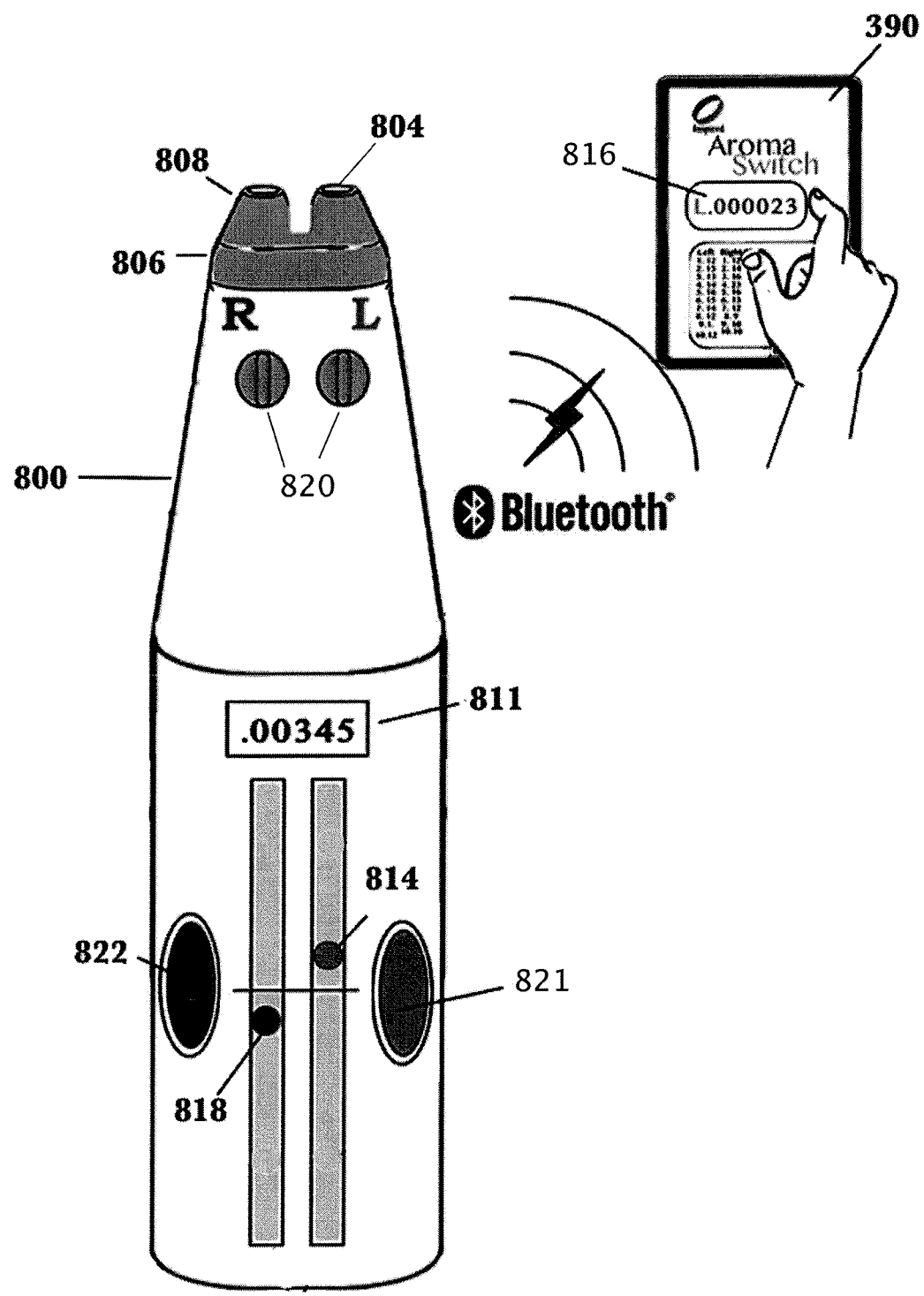
FIG. 16 illustrates a front side view of one embodiment of the present invention.

FIG. 16 illustrates a system comprising a dual nostril device 800 similar to device 700 but with additional functionality. Thus, device 800 comprises a device similar to device 700 and having a left nasal tip 804, a right nasal tip 808 and right and left one-way valves 820 to assist with exhalation along an exhalation airway as previously described and left floating ball 814 and right floating ball 818 to assist in evaluating airflow to the left and right nostrils, respectively. Device 800 differs from device 700 in that it comprises an electronic nose module 806 to detect the concentration of odorant, or pure odorant, proximate the patient's nostril and as is well understood in the art, a nose concentration digital readout 816 on the computerized application 390 that records the concentration of odorant, or pure odorant, at the patient's nostril as well as the time latency for each nostril and each trial. The device 800 is connected to the computerized application 390, as illustrated, by Bluetooth®, however a hard wire connection as in FIG. 12 may also be used. The device 800 also comprises a digital readout 811 of the concentration of the odorant, or pure odorant, within either the odorant, or pure odorant, compartment or at some point within the aroma airway passage as those structures are described in connection with device 500, using a sensor to measure the concentration (not shown but as is well known to the skilled artisan). Further, device 800 also comprises left nostril switch 821 and right nostril switch 822. These switches 821, 822 enable the data for each nostril and for each trial to be sent to the computerized device 390 and captured within a database table and compared as previously discussed when all of the trials have been completed. Note in this connection that, as illustrated, the left nostril switch 821 is activated with the nose concentration measured and displayed on the nose concentration digital readout 811 as "L.000023" indicating that the left nostril has a concentration of 0.000023 units, e.g., ppm. This data is subsequently recorded in the database for possible analysis.

Color coding may be applied to the various devices and systems of the present disclosure, for example the left and right actuation switches computer interface elements and nasal tip decorations may be color coded or otherwise distinguished in order to prevent left and right confusion by the medical personnel administering the test and in all cases are preferably oriented to the patient's perspective of left and right.

FIGS. 17, 18 and 19 illustrate part of the airflow structure defined by housing 902 in a two nasal tip device 900, similar to devices 700 and 800, wherein left and right air flow meters are included with left floating ball 914 and right floating ball 918 floating within left and right airway passages respectively and within left and right airway passage windows. In this embodiment, clear air, powered by the patient's inhalation as described supra, enters the device at clear air inlet defined by the housing 902. Clear air, when the device is not activated and therefore not producing odorant, or pure odorant, may be channeled through an air port 932 and upward through, e.g., the left airway passage as illustrated and passes through a one-way valve on the way to the left nasal tip and into the patient's left nostril. Left and right actuating switches 921, 922 may be provided and similar in function to previously described elements 821, 822 in connection with device 800.

The device 900 comprises an odorant, or pure odorant, source 930 which may be an ultrasonic source or the equivalent and may be controlled by a remote controller that may be contained within a computerized application such as element 390 described previously and having connection, either hard wire or radio connectivity to the source 930. When activated, source 930 emits odorant, or pure odorant, which is drawn upward through, e.g., the left airway channel to the patient's left nostril. A similar structure and process are employed for generating odorant, or pure odorant, and presenting same to the patient's right nostril.

Figure 20:
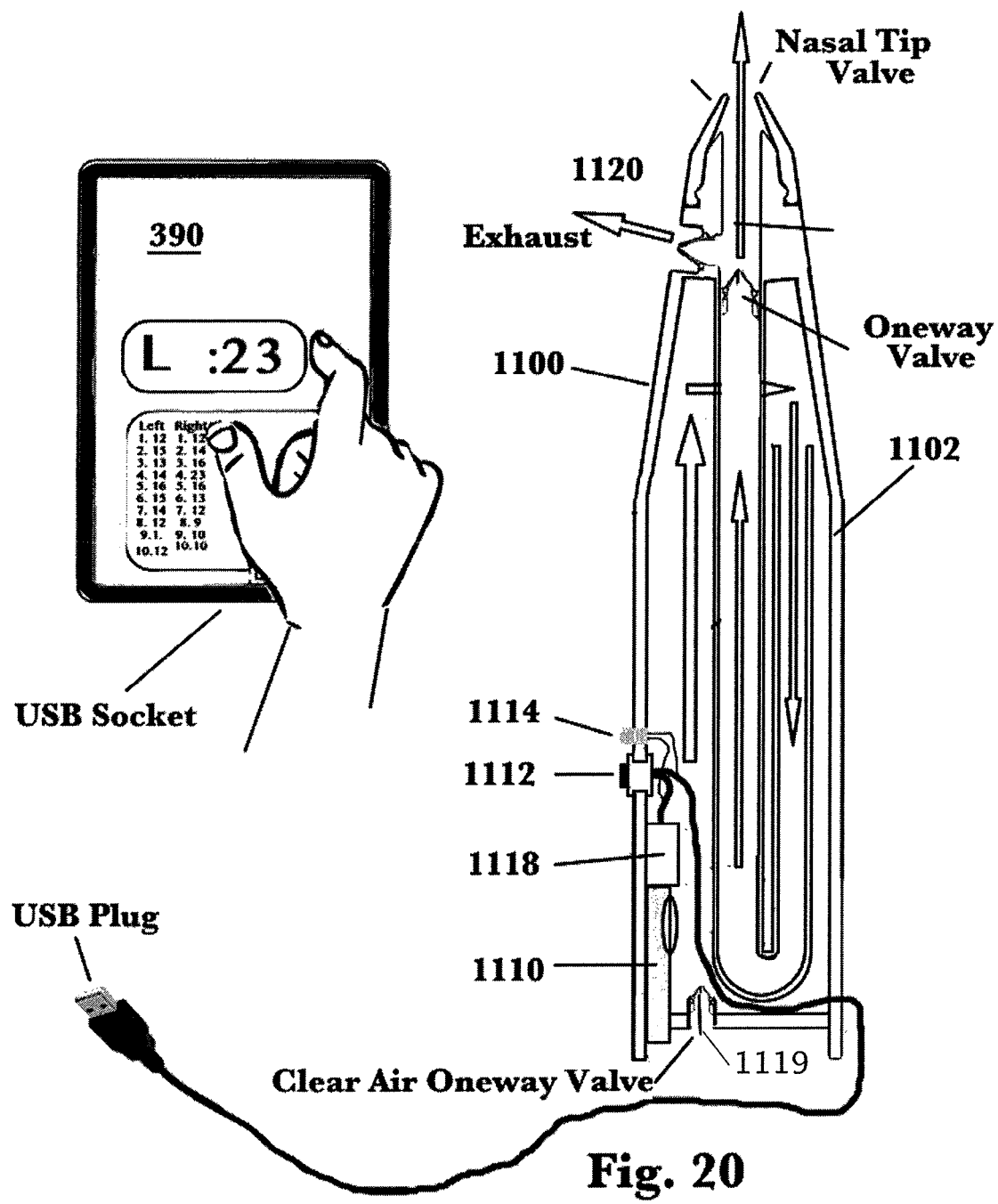
FIG. 20 illustrates a front cutaway view of one embodiment of the present invention.

FIG. 20 provides a cross-sectional view of a single nasal tip device 1100 with a USB power cord that is connected to a computerized application 390 as described earlier and which powers and, in some embodiments, controls an ultrasonic aroma emitting source 1110 which may comprise a USB male connector and which may plug into, and out of, USB female connection box 1111, electrical control (on/off) button 1112 and an indicator light 1114, powered by power source, e.g. a battery 1118. The airflow for this device 1100 is powered by the patient's inhalation force. Thus, as the patient inhales with nostril engaging nasal tip, pressure is generated that is sufficient to cause clear air to enter the clear air inlet 1119 and pass through clear air one-way valve and through the airflow chamber defined by housing 1102. In this embodiment, the aroma airway passage and the clear airway passage are combined into a single airflow chamber.

When the electrical control button is activated, the ultrasonic odorant, or pure odorant, emitting source 1110 is activated and emits odorant, or pure odorant, into the airflow chamber. As with the clear air airflow, the patient's inhalation powers the flow of the odorant, or pure odorant, infused air through the airflow chamber as indicated by the arrows, through one-way valve and into the nasal tip, ultimately into the patient's nostril.

As with prior inhalation powered embodiments, an exhalation passage is provided as illustrated by the solid line through nasal tip and out through one-way valve 1120.

Turning now to FIGS. 21-23 cross-sectional views are provided of a single nasal tip device 1200 with a USB power cord that is connected to a computerized application 390 as described earlier and which powers and, in some embodiments, controls an ultrasonic aroma source 1210 which may comprise a USB male connector and which may plug into, and out of, USB connection box 1211, an electric actuation button 1212, an actuator button 1213 and an indicator light 1214. The airflow for device 1200 is powered by the patient's inhalation force. Thus, as the patient inhales with nostril engaging nasal tip as in FIG. 23, force is generated to cause clear air to enter the clear air inlet 1250, pass through clear air inlet one-way valve 1252 and through the clear airflow passage or chamber 1270 defined in part by housing 1202 through one-way valve to the nasal tip and into the patient's nostril. The clear airflow passage or chamber is, in part, flexible and able to move in concert with the actuator button 1213 as it is depressed to activate the device 1200 and its odorant source 1210. Thus, as seen in FIGS. 21 and 23, the air passage above the clear air inlet 1250 is substantially straight, with a clear path to the nasal tip.

However, when actuator button 1213 is depressed as indicated by the arrow in FIG. 22, the flexible portion 1280 of the clear airflow passage or chamber disconnects from the non-flexible portion 1281 of the clear airflow passage or chamber and shifts laterally, as shown to the right, the length of the travel of the button 1213 as it is depressed. This is enabled by a fixed attachment of the flexible portion 1280 to the actuator button 1213 which therefore requires its concomitant lateral movement. This lateral shift, as indicated in FIG. 22, blocks off the clear air pathway and activates the odorant, or pure odorant, passage or pathway 1271, allowing odorant, or pure odorant, infused air to travel through aroma air inlet 1260 and one-way valve 1262, into odorant compartment 1264 where the air becomes infused with odorant or pure odorant. The aroma or odorant infused air then flows through the device as illustrated to the nasal tip and into the patient's nostril. This air flow pathway comprises the aroma airway passage. Releasing button 1213 allows flexible portion 1280 to realign with non-flexible portion 1281, recreating the clear air passage.

When actuator button 1213 is depressed as indicated by the arrow in FIG. 22, electrical actuation button 1212 is activated which, in turn switchingly activates the ultrasonic odorant, or pure odorant which emits odorant, or pure odorant, into the airflow chamber. As with the clear air airflow through the clear airway passage, the patient's inhalation powers the flow of the odorant, or pure odorant, infused air through the aroma airway passage as described above.

As with prior inhalation powered embodiments, an exhalation passage may be provided as illustrated by the solid line through the side nasal tip and out through one-way valve 1220 as shown in FIG. 21 in exhalation mode initiated by the patient exhaling into a nasal tip.

Figures 24, 25:
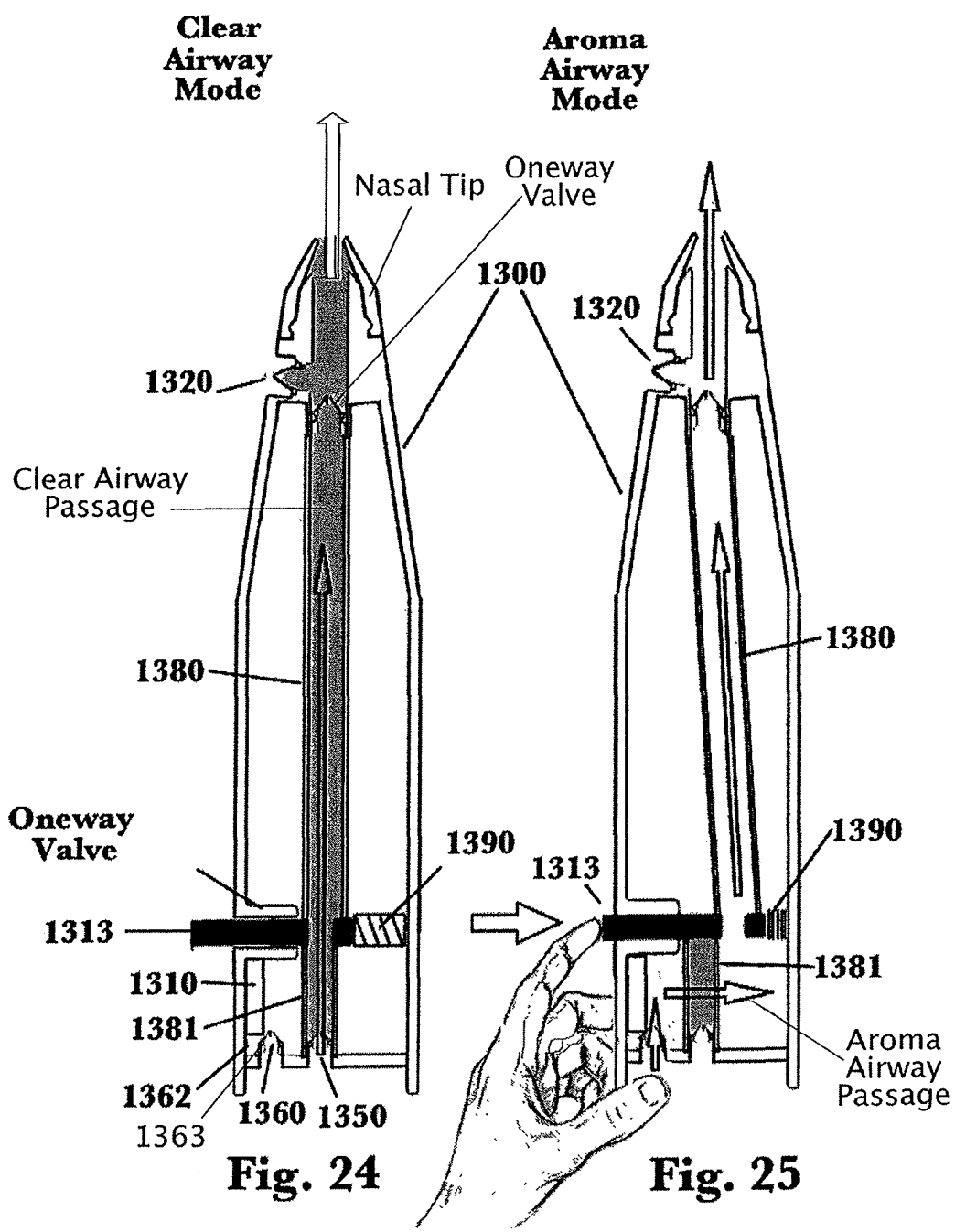
FIG. 24 illustrates a cutaway view of one embodiment of the present invention.
FIG. 25 illustrates a cutaway view of one embodiment of the present invention.

FIGS. 24 and 25 are the same structurally as the device of FIGS. 21-23, with one exception. A biasing spring 1390 is provided to provide biasing force to actuator button 1313, actuator button 1313 in an unactivated position as in FIG. 24. In this case, the clear airway passage is open, when patient inhales clear air is taken into the clear air inlet 1350 and through one-way valve 1363 and drawn up through the clear air passage, through the one-way valve into the nasal tip and into the patient's nostril.

When force sufficient to overcome the spring's biasing force is applied, the button 1313 depresses and activates the device 1300 as in FIG. 25. The ultrasonic odorant, or pure odorant, source 1310 is switchingly activated in the same manner as that element is activated as described in connection with FIGS. 21-23. As in FIGS. 21-23, a flexible portion of the passageway 1380 is attached to the button 1313 and flexes or moves laterally with the movement of button 1313, disconnecting from the non-flexible portion 1390 and ultimately blocking the clear airway passage as shown in FIG. 25 and switchingly creating an aroma airway passage. This allows inhalation force provided by the patient to draw clear air into the aroma air inlet 1360 and one-way valve 1363 and into odorant chamber 1362 and move through the device 1300 as indicated through the flexed portion 1380 and one-way valve to the nasal tip and into the patient's nostril. Releasing the button 1313 reconnects flexible portion 1380 with non-flexible portion 1390.

As with prior inhalation powered embodiments, an exhalation passage may be provided as illustrated by the solid line through the side nasal tip and out through one-way valve 1320 as shown in FIG. 21 in exhalation mode initiated by the patient exhaling into the nasal tip.

Figures 26, 26A, 26C:
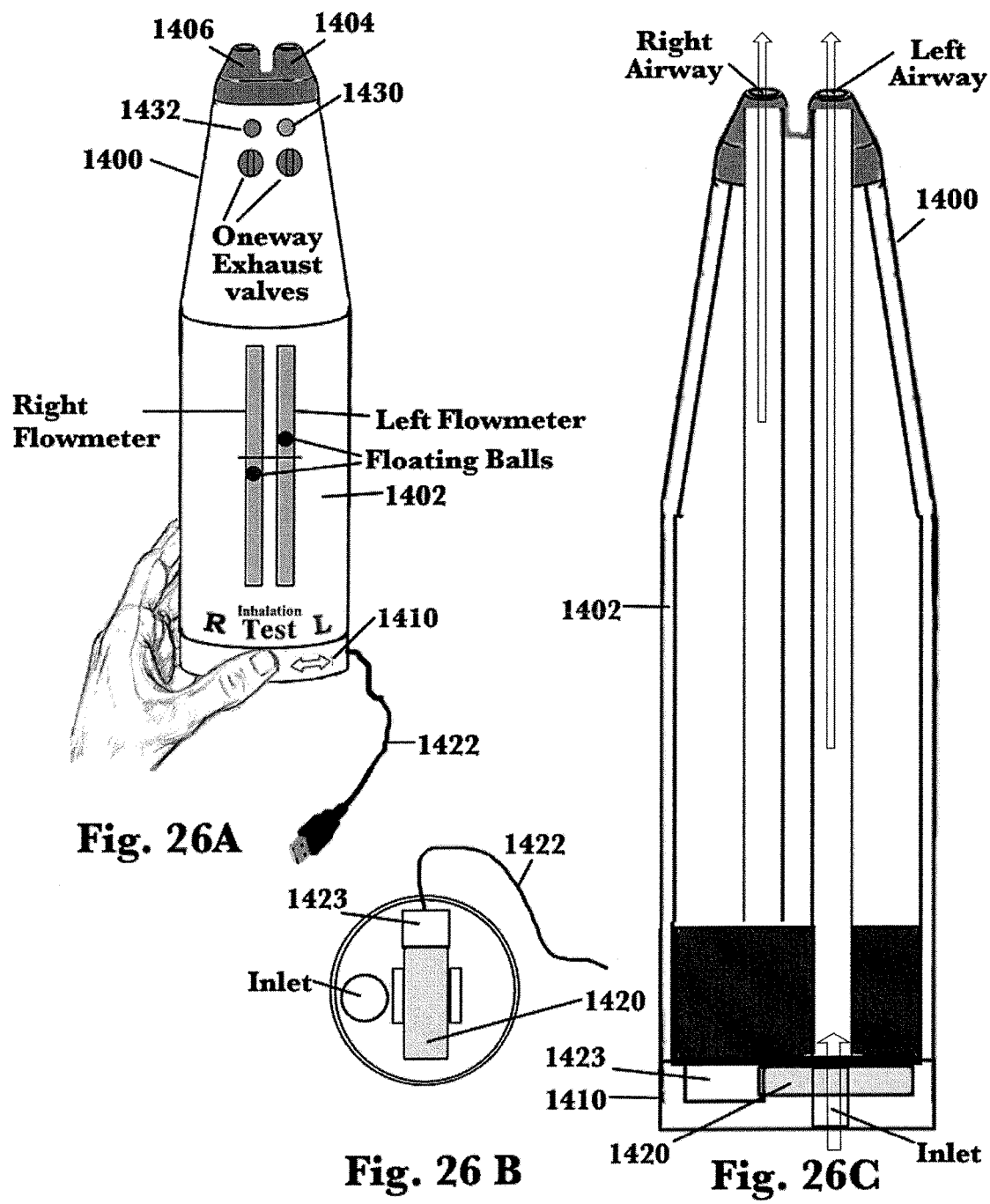
FIG. 26A illustrates a front view of one embodiment of the present invention.
FIG. 26C illustrates cutaway view of one embodiment of the present invention.

FIGS. 26A, 26B and 26C illustrate a dual nasal tip inhalation-driven embodiment 1400 wherein the switching mechanism between a clear airway passage and an aroma airway passage is achieved using a rotating base 1410 in combination with an odorant source 1420, as illustrated odorant source comprises an aroma emitting device in communication with a USB cord 1422 and associated computing device (not shown) but as previously described. Thus, rotating base 1410 rotates relative to the housing 1402 of dual nasal tip device 1400 into at least two positions: Right and Left.

The odorant source 1420 is arranged and fixed horizontally within rotating base 1410 as shown in FIG. 26B, with USB cord 1422 connected thereto to enable remote, or external, activation of the source 1420 by a computerized implement such as a programmable computer device. Left and right nasal tips 1404, 1406 are arranged on housing 1402 as shown, each tip 1404, 1406 having a lumen therethrough and in communication with left airway and right airway as shown. Rotating base 1410 comprises an inlet for enabling air to enter one or both of the left and/or right airways when the user applies inhalation force to the nasal tips 1404, 1406.

Thus, when the rotating base 1410 is in the Left position as shown, odorant source 1420 is aligned only with the left airway and in fluid communication therewith so that, upon application of inhalation force by the user, air is drawn into rotating base 1410 through inlet where it becomes infused with the odorant from odorant source 1420. In this position, odorant infused air flows through only the left airway, but not the right airway which may be blocked so that the aroma airway passage is restricted to the left nostril. Alternatively, only clear air may flow through the right airway to the right nostril, thereby creating a clear air pathway, when device is in the Left position.

Alternatively, when the rotating base 1410 is rotated to the Right position as, odorant source 1420 is aligned only with the right airway and in fluid communication therewith so that, upon application of inhalation force by the user, air is drawn into rotating base 1410 through inlet where it becomes infused with the odorant from odorant source 1420. In this position, odorant infused air flows through only the right airway, but not the left airway which may be blocked so that the aroma airway passage is restricted to the left nostril. Alternatively, only clear air may flow through the left airway to the left nostril, thereby creating a clear air pathway, when device is in the Right position.

The illustrated embodiment comprises a left airflow meter and a right airflow meter, each meter comprising a floating ball in communication with the left and right airways as a method for assessing relative airflow through each of the left and right airways. This structural arrangement is described above. In addition, left annunciator 1430 and right annunciator 1432 are operatively connected with the rotating base 1410 and a power source (not shown but as is well known to the skilled artisan) and capable of selective lighting to enabling visual indication of the airway passage (right or left) that is active at any given time.

Figures 27A, 27B:
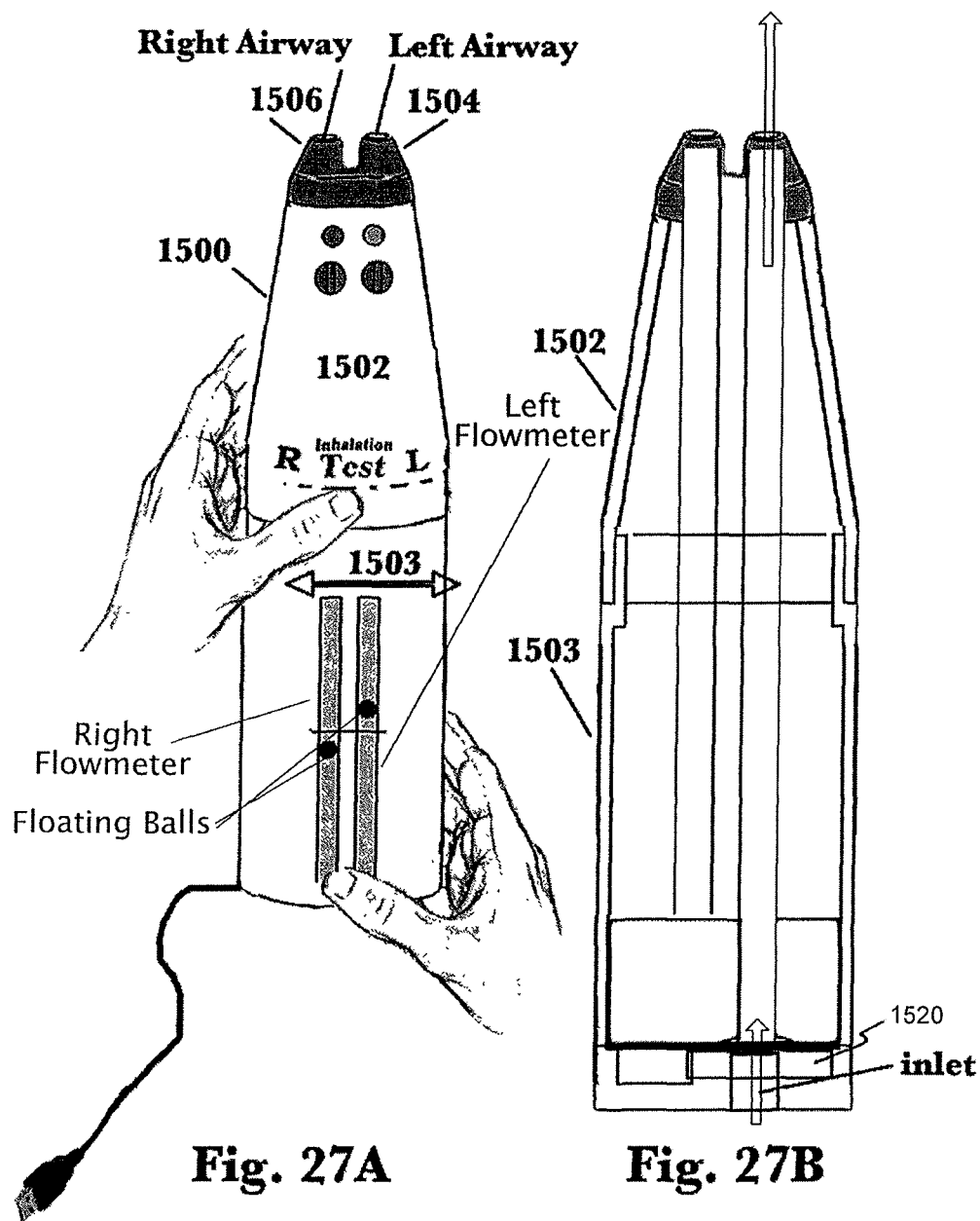
FIG. 27A illustrates a front view of one embodiment of the present invention.
FIG. 27B illustrates a cutaway view of one embodiment of the present invention.

FIGS. 27A and 27B provide an alternative embodiment 1500 to the device of FIGS. 26A-26C. Here, housing 1502 is rotatingly engaged with a rotating lower section 1503, rather than the rotating base of FIG. 26A, to accomplish the switching between right and left airways and aroma airway passage and (in certain embodiments) clear airway passage. Thus, 1502 remains stationary while rotating lower section 1503 rotates between Left and Right positions, wherein the odorant source 1520 is in fluid communication with either the left airway or the right airway.

Figure 28:
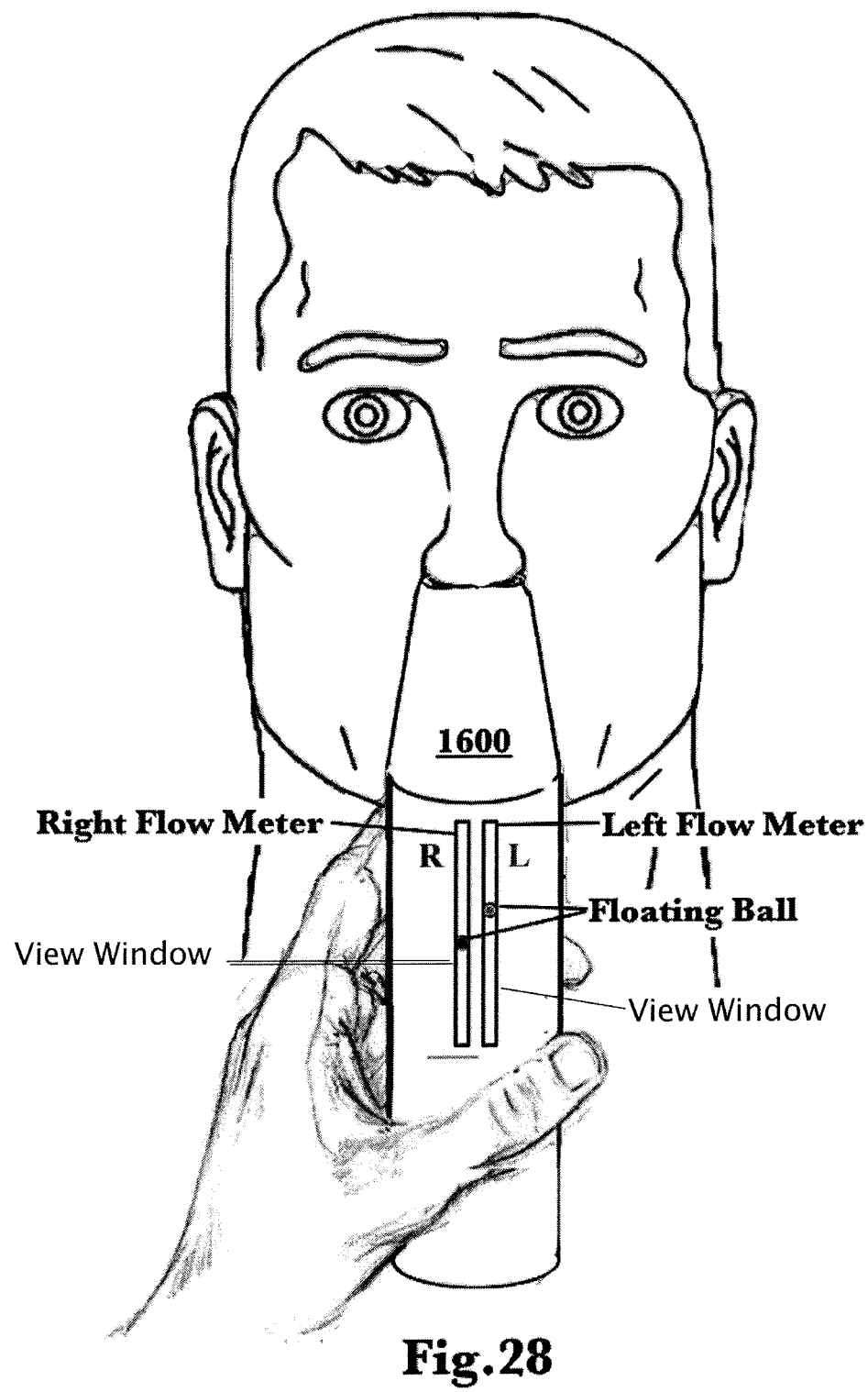
FIG. 28 illustrates a front view of one embodiment of the present invention.

Turning now to FIG. 28, a device 1600 is provided to assess the efficiency of the patient's right and left nasal inhalation ability. As described supra, the patient inhales through the nasal tips, creating an airflow through the device and activating floating balls within the right and left airflow meters, floating balls being visible through viewing windows. This allows for a visual assessment of the patient's relative ability to inhale, i.e., left vs right, as well how that visual assessment data compare with an established baseline inhalation ability. The baseline may be derived from prior experiences with the patient and the test device 1600 and/or may be derived from average population inhalation capability statistical data. This may be part of a pre-assessment test conducted, together with evaluation of any structural nasal or other abnormalities that may inhibit inhalation ability, either on a unilateral (left or right) or a bilateral (right and left) basis. This device 1600 does not comprise an odorant source and is only intended to serve as an assessment tool. Left and right flow meter balls may be color coded, or otherwise distinguished or marked, as described above to prevent left and right confusion by testing personnel who may be entering air flow data into a computing device, accessory or appliance, which may also be similarly color coded or comprising markings or letters that distinguish left nostril data from right nostril data.

Generally, the device of FIG. 28 comprises a housing, the housing comprising:

a right nasal tip having a lumen therethrough as, e.g., in the device of FIG. 27A;

a left nasal tip having a lumen therethrough as, e.g., in the device of FIG. 27A;

a right airway passage in fluid communication with the right nasal tip as, e.g., in the device of FIG. 27A and in communication with an air source, e.g., ambient air;

a left airway passage in fluid communication with the left nasal tip as, e.g., in the device of FIG. 27A and in communication with an air source, e.g., ambient air;

a right airflow meter in fluid communication with the right airway passage the right airflow meter defining a viewing window through the housing and a first floating ball therein as those structures are defined supra;

a left airflow meter in fluid communication with the left airway passage, the left airflow meter defining a viewing window through the housing and a second floating ball therein as those structures are defined supra, wherein, when the patient inhales, the airflow through the right and left airway passages causes the first floating ball to rise to a level commensurate with the air pressure generated by the inhaling patient's right nostril and further causes the first floating ball to rise to a level commensurate with the air pressure generated by the inhaling patient's left nostril, the floating ball levels viewable through the housing window.

Figures 29A, 29B:
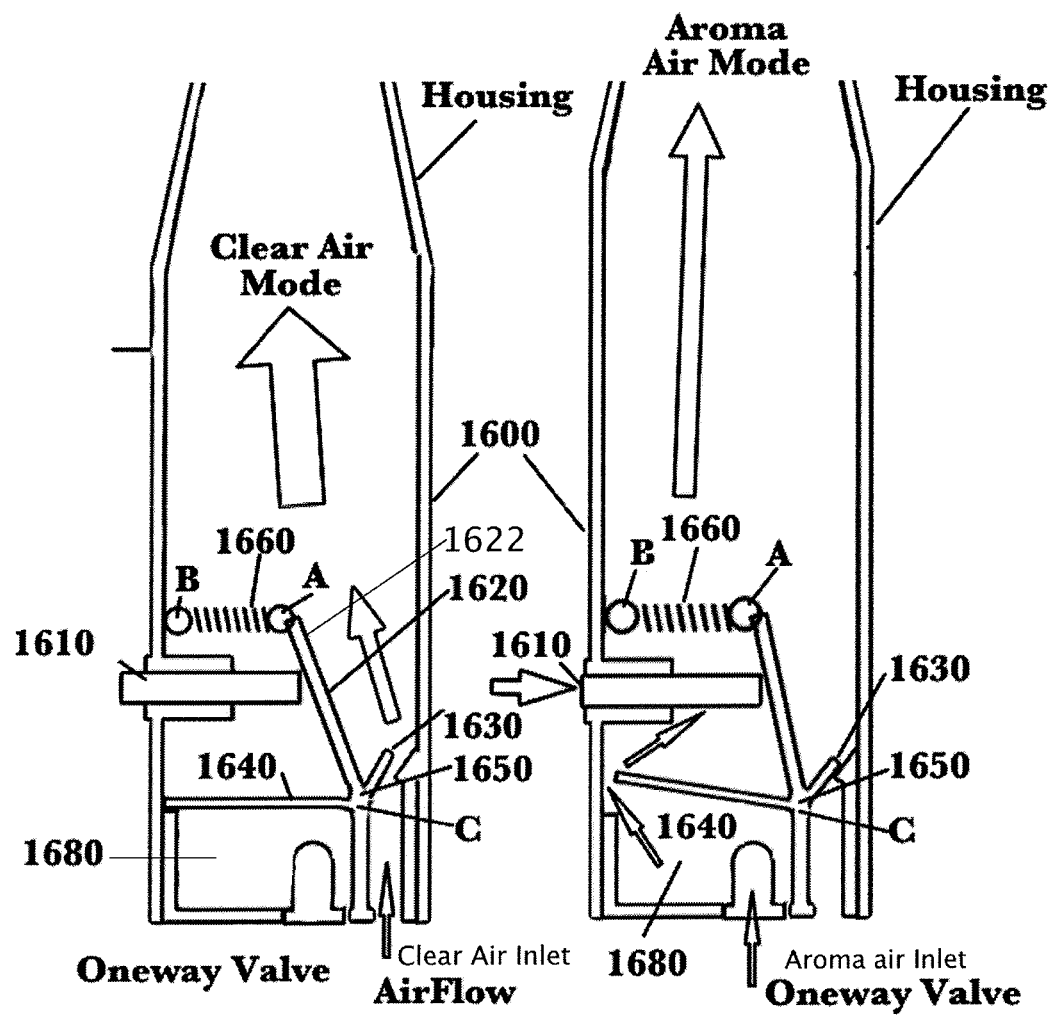
FIG. 29A illustrates a cutaway view of one embodiment of the present invention.
FIG. 29B illustrates a cutaway view of one embodiment of the present invention.

FIGS. 29A and 29B illustrates cutaway an alternative switching mechanism 1600 within housing of any of the devices described herein and that may be applied to any preceding embodiment described herein to switch between a clear airway passage comprising no odorant-infused air, and an aroma airway passage comprising odorant-infused air.

Thus, actuator 1610 is illustrated as slidingly and operatively communicating with housing and with actuating arm 1620 of butterfly valve 1650. Distal end 1622 of actuating arm is in fixed communication with one end A of spring 1660 and in operative communication with actuating arm 1620, wherein the other end B of spring 1660 is fixed to housing. Spring 1660 presents a biasing force tending to pull actuating arm 1620 toward housing.

Butterfly valve 1650 comprises three arms: the actuating arm 1620 described above, a clear air arm 1630 and an aroma air arm 1640, each of the arms 1620, 1630, 1640 are pivotable about an axis, represented by C. Aroma air arm 1640 is biased by the spring 1660 to the closed position of FIG. 29A while clear air arm 1630 is concurrently biased by the spring 1660 to the open position of 29A. In this biased position, the clear air passage is open while the aroma air passage is closed. An odorant source compartment 1680 is defined by the housing, comprising an odorant source therein as discussed supra, and, when closed, by the aroma air arm 1640 which controls whether air infused with the odorant may enter the air flow through the device and ultimately to the user's nostril(s).

The biasing force of spring 1660 may be overcome by application of force on actuator 1610 in the direction of the arrow in FIG. 29B, depressing actuator 1610 into the housing and, in turn, applying force to the actuating arm 1620 of butterfly valve 1650. As a result, and as shown, spring 1660 is expanded and butterfly valve 1650 rotates about axis C. This causes clear air arm 1630 to close against housing, restricting all flow through the clear air passage of FIG. 29A, while aroma air arm 1640 rotates upward and away from the housing and the closed position of FIG. 29A to the open position and switching to the aroma air passage of FIG. 29B.

Thus, FIG. 29A illustrates the butterfly valve 1650 in a position to open the clear airway passage and close the aroma airway passage, trapping the odorant, or pure odorant, molecules of the odorant source within the odorant source compartment 1680. FIG. 29B illustrates the butterfly valve 1650 in a position to close the clear airway passage and open the aroma airway passage.

Figures 30A, 30B:
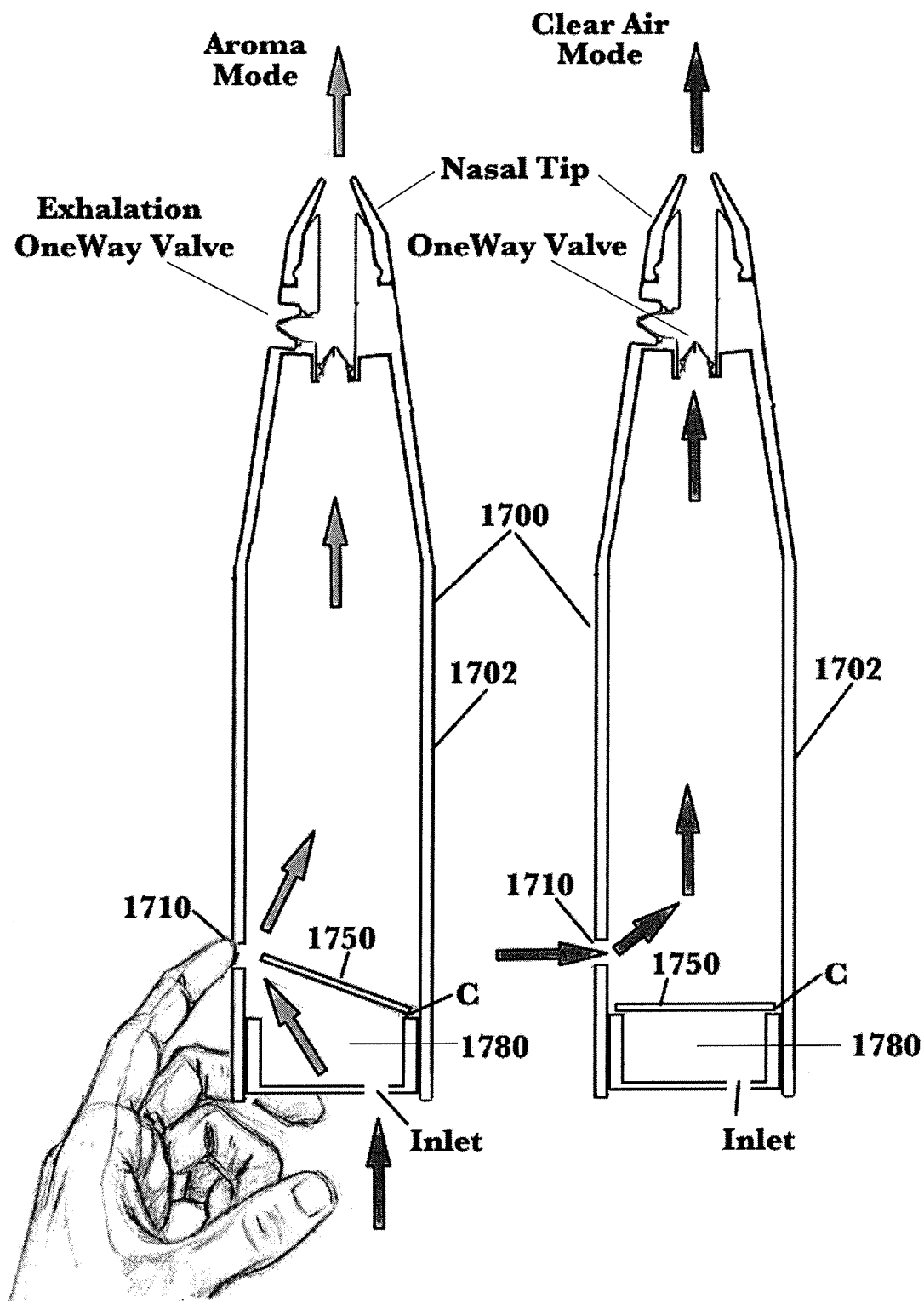
FIG. 30A illustrates a cutaway view of one embodiment of the present invention.
FIG. 30B illustrates a cutaway view of one embodiment of the present invention.

FIGS. 30A and 30B provide another alternative to the switching mechanism enabling switching between a clear airway passage and an aroma airway passage. Thus, device 1700 comprises housing 1702, wherein housing defines an inlet for clear air to enter housing, a closeable orifice 1710 and, together with flap valve 1750, odorant source compartment 1780. Thus, when orifice 1710 is open, i.e., uncovered as in FIG. 30B, clear air enters orifice 1710 upon application of inhalation force by the user, flows through the housing, through one-way valve and outward through nasal tip as described supra. Odorant source compartment 1780 is closed in this instance, as flap valve 1750 is closed against housing and no infused air is allowed to enter the resulting clear airway passage.

However, when orifice 1710 is closed, as by covering substantially completely with the user's finger as shown, and the user applies inhalation force to the nasal tip, clear air flows into the housing through inlet, opening flap valve 1750 and the air flowing through the odorant source compartment 1780 becomes infused with odorant from the odorant source therein. The infused air flows upwardly and through the nasal tip as described supra.

As with prior inhalation powered embodiments, an exhalation passage may be provided as illustrated by the solid line through the side nasal tip and out through one-way exhalation valve as shown in FIG. 21 in exhalation mode initiated by the patient exhaling into a nasal tip.

Figure 31:
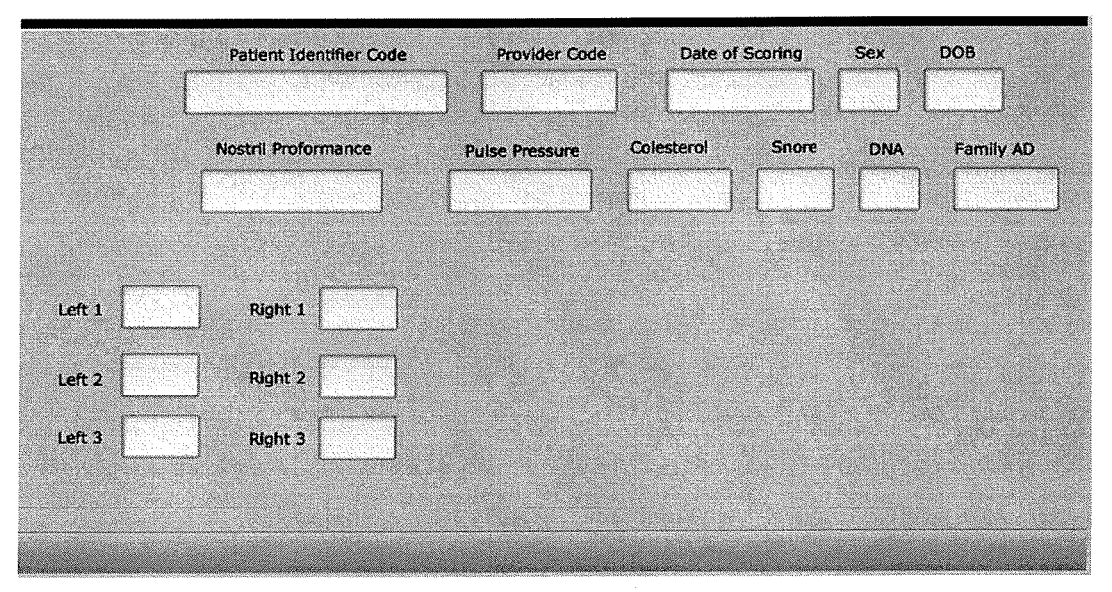

Turning now to FIG. 31, one manual method of recording trial results using the various embodiments of the present invention is provided. Here, the patient's name, date of birth, test event name, relevant medical history, relevant physical assessment observations, blood pressure, cholesterol levels and other risk factors for, e.g., AD, in addition to nostril airflow pre-test results, when administered, and aroma scale results are optionally recorded. Further, spaces for 1-10 trials are provided, separately for the right nostril and the left nostril. Finally a ratio of the summation of the left nostril trial data over the summation of the right nostril trial date is calculated to obtain the patient's disease risk "score". The ratio may be then evaluated for significant differential between the nostril trial data, e.g., in the case of an Alzheimer's patient, the ratio will be greater than 1. More preferably, the ratio in this case will be greater than 1.1, and still more preferably greater than 1.25.

Figure 32:
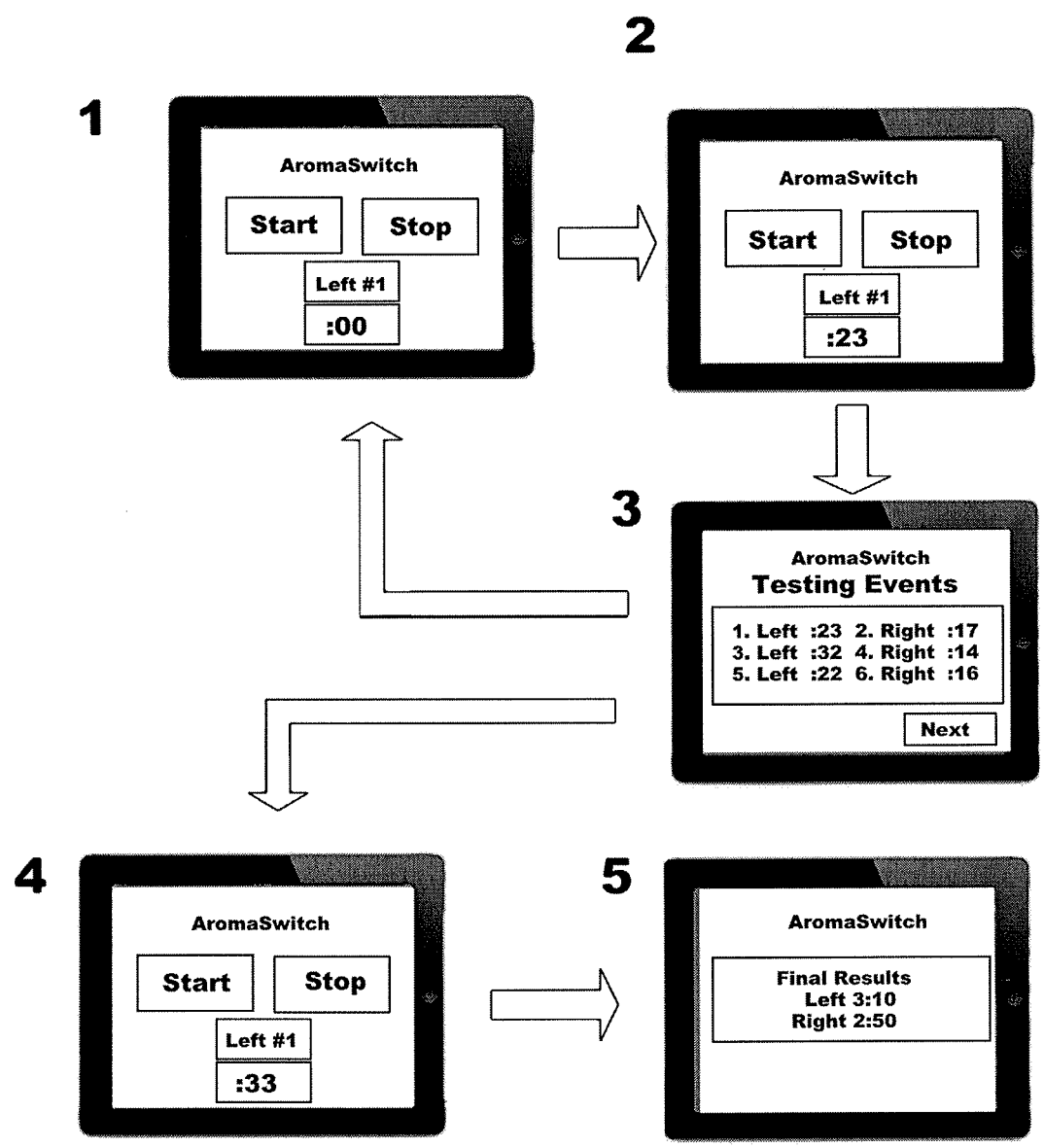
FIG. 32 illustrates an application for data entry and/or capture and analysis for use with the present invention.
Figure 33:
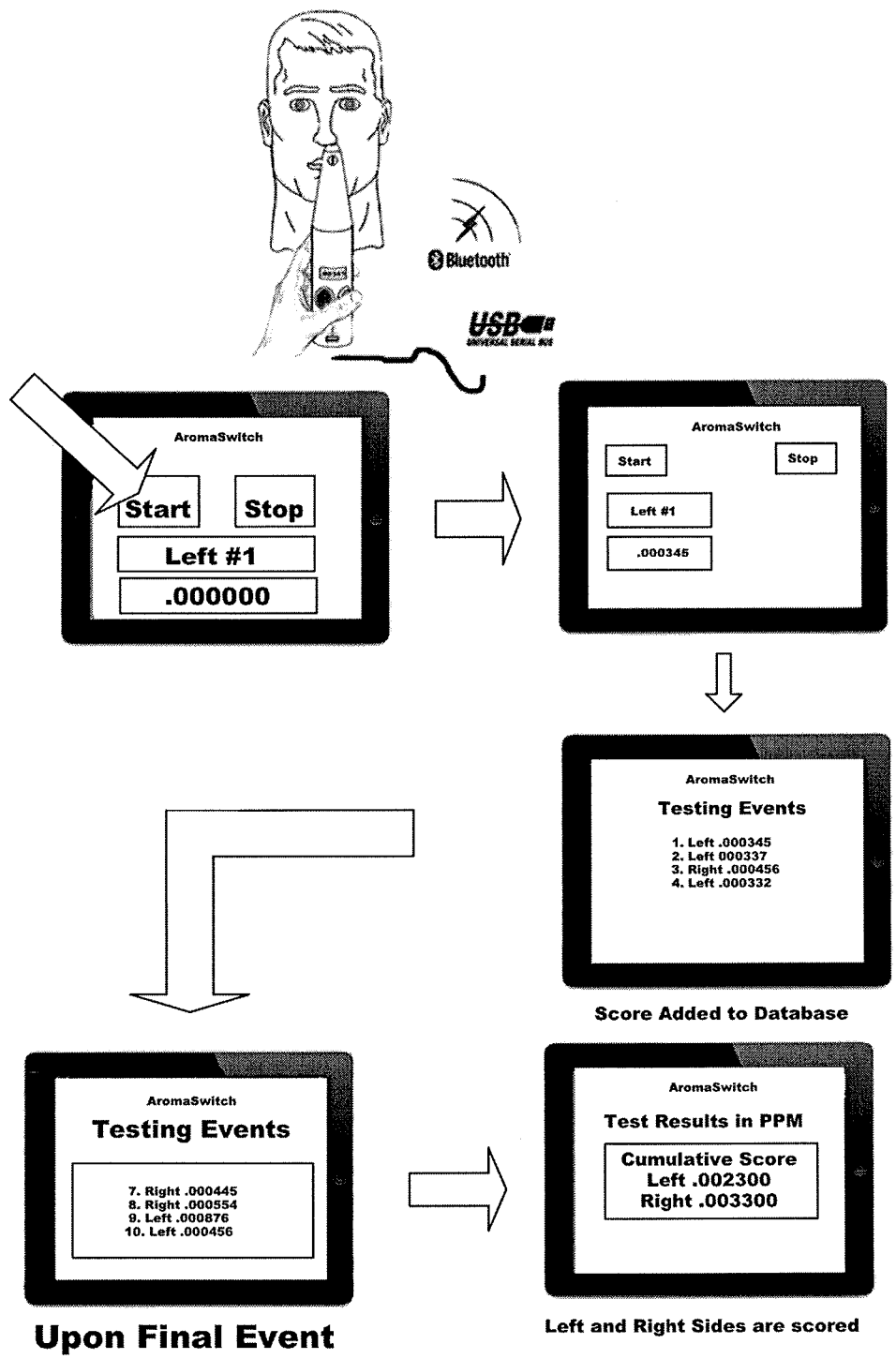
FIG. 33 illustrates an application for data entry and/or capture and analysis for use with the present invention.

A computerized application and alternative embodiment of the method of FIG. 31 is provided in FIGS. 32 and 33. Here, the data may be entered by hand into a spreadsheet previously created and saved within the memory of a programmable computing device, accessory or appliance such as previously described or may be automatically communicated by, e.g., a USB device as described herein that is connected to the testing device and in communication, i.e., wired or wireless, with the computing device. In addition, the computing device can control the testing device in terms of stopping and starting aroma presentations. Thus, in blocks 1 and 6, the left nostril trial number 1 is initiated by pressing the start button whereupon the associated testing device switches into aroma airway mode for the left nostril. When the user notifies of the presence of an aroma in his or her left nostril, the stop button is hit as in blocks 2 and 7 and the testing device stops delivering aroma or odorant. This is repeated for the right and left nostrils in a preferably random manner using, e.g., a random left vs. right generator function, until the requisite number of trials for each nostril is complete, with the scores added to a database as shown in blocks 3 and 8. Block 4 indicates another trial for the left nostril to be added to the database of block 3. Ultimately, the required number of trials for each nostril is completed as shown, e.g., in block 9, and the preprogrammed instructions for the application shown provide summary statistics as in blocks 5 and 10. Here, the raw summation of the left vs right trials are shown. Alternatively, or additionally, the ratio of left over right summation data, or right over left summation data, may be shown. Still further, known statistical techniques may be employed to, e.g., remove outlier data and the like to arrive at a robust statistical comparative result. Block 10 completes a comparison of the data and recognizes a deficit of the summed trial data of the left nostril vs the right nostril.

Moreover, a software database and testing protocol support application(s) may be used to achieve the testing described herein with any of the disclosed device and system embodiments of the present invention. The software database may be within individual computing devices and/or may be housed within a central server that is interconnected with individual computing devices that are located at testing sites. One embodiment of this interconnected system is provided in FIG. 34. As illustrated, at least one central server is provided and in communication with at least one remotely located computing device. Central server(s) may be cloud-based which may permit controlled access from any internet connected device, preferably a secure account enabled internet connection is employed.

Figure 34:
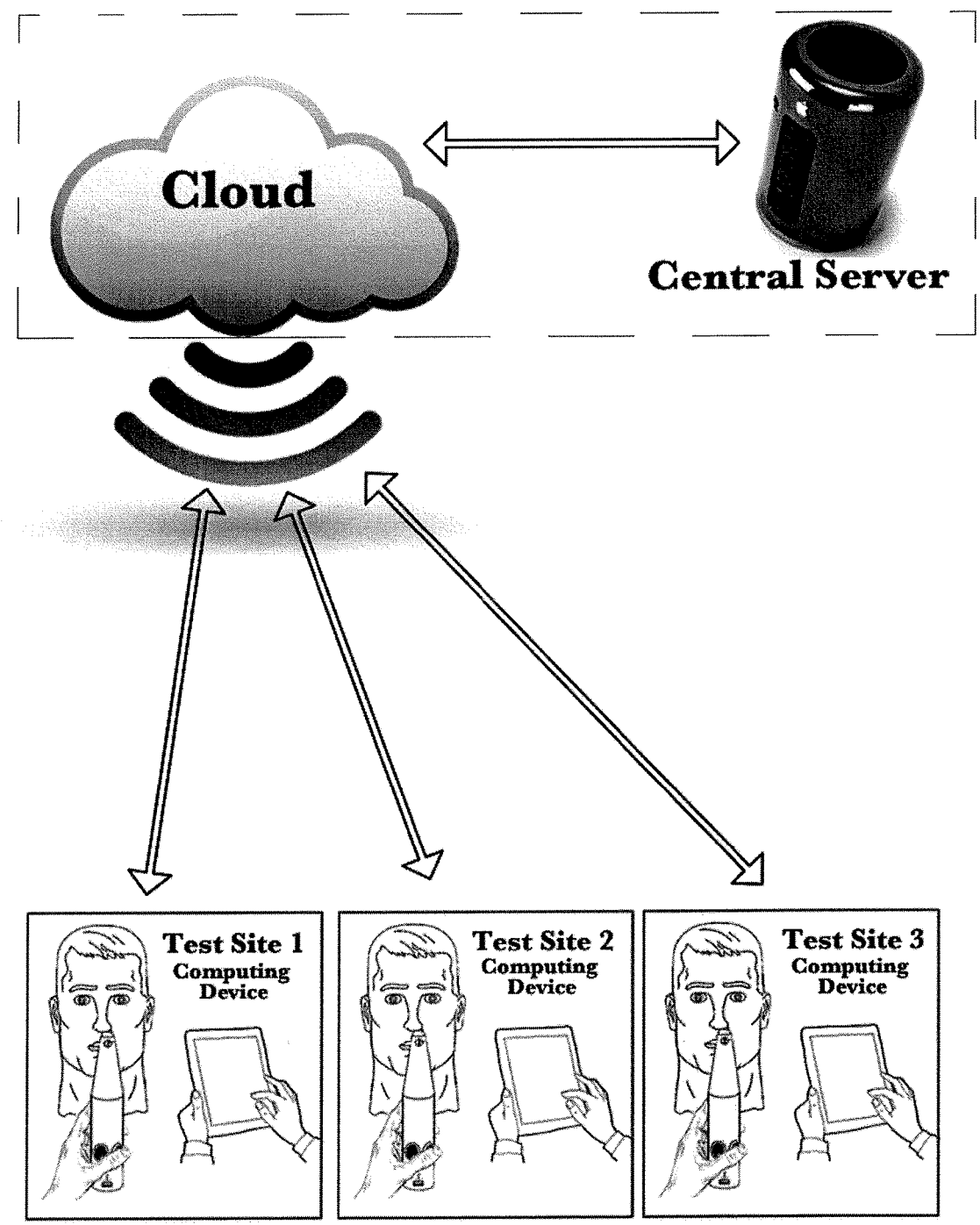
FIG. 34 illustrates a block diagram of one embodiment of a method and system of the present invention.

The programmable computing device of FIG. 34 comprises: a memory, wherein the application, including programmed instructions for running the test protocol embodiments described herein is stored and for storing test results; a processor operatively connected with the memory and which executes the application and associated programmed instructions; a display that may display the application, test data results for left and for right nostril trials, trial number, a timer and the final calculated results in terms of any differential between the left and the right nostril detection thresholds, or a differential between a previous baseline or population statistical average score, and the instant test score. The display is operatively connected with the processor and memory; and a transmitter and a receiver for operatively connecting, and communicating with, the central server. In this system, the testing results may be obtained at the testing sites and added, either manually or automatically as described herein, to the computing device for storage and possible transmission of the data to the central server.

When the testing procedure is complete, the test data may be sent, either automatically or upon prompting by the user, from the computing device at the associated test site to the remote central server. Central server comprises a memory for storing the received test data from the at least one computing device and associate test site(s) and for storing an algorithm for processing and analyzing the instant test site results; a processor for executing the programmed instructions within the stored algorithm; a transmitter and a receiver operatively connected with the at least one computing device whereby two-way communication with the at least one computing device is enabled. Central server's memory further comprises a database for storing all of the test results received from the at least one computing device which may be used to develop further refined and more robust statistical conclusions regarding relevant elements of the patient's medical history and the instant test data received from the at least one computing device for an individual patient and securely transmit the calculated disease risk score based at least in in part upon global data stored within the memory of the central server and reported to the local computing device. Robust encryption and security features may be employed to protect individual patient's privacy rights.

This refinement will thus enable, e.g., a progressively more robust test result that may allow detection of a significant differential or change in the test data for an individual patient. For example, early onset of Alzheimer's disease may be detected progressively earlier as the database becomes more populated to eventually become a vast library of relevant medical history and patient test data and, as a result, becomes more robust. Thus, certain embodiments of the database of the central server may allow analysis of the data within the database for generation of the smallest possible differential in the olfactory threshold values, left vs right, that is still clinically significant. This is the point at which the device, systems and methods of the present invention will allow earliest possible detection of asymmetry and, in turn, earliest possible detection of Alzheimer's disease.

Similarly, in the case of symmetrical olfactory dysfunction, the database of the central server may be analyzed to determine the smallest change, from either baseline or from a prior test point or from a population statistical average, that may be considered clinically significant. This represents the finest analysis and diagnosis possible for symmetric olfactory dysfunction and the ability to monitor the underlying condition or disease progression and/or the efficacy of the treatment regimen.

The algorithm of the central server may analyze the data received from the at least one computing device and, when analysis is complete, the central server may transmit an electronically secure summary of the testing results as a risk score as described above back to the computing device at the test site so that the user, i.e., a health care provider, can observe the results by, for example, a secure email sent to a predetermined email address.

In addition, a separate application or, alternatively, an internet browser supported client program may supply a checklist of a patient's pre-testing history and enable establishing of the patient's clinically acceptable baseline of nasal performance, including any relevant medical history factors such as structural or medical issues that may compromise the left or the right nostril/airway performance and/or efficiency. This baseline value may be incorporated into the above algorithm to provide a corrective factor that essentially treats any observed airway performance for the left and/or right nostril and associated airway as a variable that may skew the final results if not corrected. The database described above may also accept input of this data and incorporate it into the analysis phase to enable a corrected result to be calculated and typically securely communicated to the appropriate computing device and associated test site.

As described above, certain embodiments of the disclosed devices of the present invention comprise measurement of the concentration of the odorant, or pure odorant, presented to the patient's nostrils that are required to evoke a response by the patient, i.e., an indication that the odorant, or pure odorant olfactory threshold was reached. In this case, the data tables or databases as described in FIGS. 30-32 may comprise concentration data in the form of, e.g., parts per million (ppm) that is equivalent to the olfactory threshold, with further analysis based on that concentration data either within the computing device application and/or at the central server(s) as described above.

Still further embodiments may capture the number of breaths a patient requires to inhale through the various devices and methods of the present invention to reach the olfactory threshold for each nostril. The breath data may be captured and analyzed as in FIGS. 30-32, for example, by the computing device application and/or at the central server(s) as described above.

A combination of data types may be obtained using the devices and methods of the present invention, e.g., capturing the elapsed time between introducing aroma to the aroma airway passage and the detection thereof by the patient, the number of breaths required to detect the introduced aroma and/or the absolute concentration of odorant, or pure odorant, required to reach the olfactory threshold for each nostril. The data may be analyzed by the local computing device's application and/or analyzed remotely at the central server(s) as described above in order to determine the patient's odorant, or pure odorant, detection threshold.

In certain embodiments, the testing protocol may be accomplished using the various devices and systems of the present invention described above by slowly increasing the concentration of aroma until the trigger point of cognitive notice is reached. This may be done by measuring the time it takes to recognize an increasing aroma level. Similarly, the number of inhalations required during a testing event required to detect the aroma may be significant, simple and useful measurable standard.

In an alternative embodiment, an absolute aroma concentration testing method, a real time digital "electronic nose" measurement of the actual parts per million of pure aroma per a known volume of breathable gas may be used. The aroma concentration is slowly increased to reach the required minimum saturation level required to trigger the pure aroma detection threshold. That digital value becomes a data point for the nostril being tested. A test event result might be based upon an average of, e.g., 0.000340 ppm on the left side and 0.000580 ppm on the right side. The ppm score can be converted to a L/R ratio such as, 0.000340/0.000580 or some other mathematical notation suitable for statistical analysis and reporting the data in a useful form to a health care provider.

Certain laboratory testing equipment is able to accurately identify and quantify a very specific aroma or exact sets of specific aromas in real time and displayed concentrations digitally in parts per million. These electronic smelling devices are well known to the skilled artisan. Electronic nose modules are thus very sensitive, but only detect a very narrow range of organic or chemical odor that they are "fingerprinted" to detect.

Using electronic nose modules in a bilateral clinical aroma detection threshold testing device is disclosed. As the concentration of a pure aroma in a breathable gas is slowly increased, a realtime digital readout slowly rises numerically, until the subject notes in cognitive recognition that an aroma is detected. The numerical readout may be automatically fixed or frozen at the level required for cognitive notice that an aroma has been detected when the test administrator removes their finger from the aroma control button.

The clinical testing personnel notes the ppm displayed which was required to elicit the reaction and also notes which nostril was being tested by that particular testing event. Data record keeping may be accomplished, as described herein, by a computer attached by USB or wire or radio system such as BlueTooth or WiFi, to the testing device or testing results may be scored and calculated on paper.

Taking a clinically accepted baseline of individual nasal air flow performance into account, reduces test error and enhances the overall efficacy of the disclosed aroma test. If a person has a severely reduced airflow in one nostril, without taking that issue into account, test results might be skewed. Below are at least some of the ways to validate a clinically suitable "baseline of nasal performance".

Relative airflow measurement of the nostrils overcomes most inhalation air volume impediment variables or at least make the testing personnel visually and/or graphically aware of the issue in a quantitative way. Direct airflow testing with dual gas flowmeters, visually comparing the actual inhalation volume of the two nostrils at the same time, is certainly the most important consideration for establishing a nasal performance baseline. A bilateral inhalation airflow testing device, herein disclosed, e.g., in FIG. 28, has two airflow readout elements displayed side by side to visually compare the nasal inhalation performance of the two nostrils, wherein the testing and comparing is accomplished at the same time for the two nostrils.

The subject may be shown the readout in a mirror and is asked to inhale gently such that the top ball is near a mark on the readout. The ball that is constantly lower indicates that the indicated nostril has a lower airflow volume. A bleed valve might be provided to "set" the upper limits and calibrate the readout at the factory. An airflow inhalation testing device is built into some embodiments of the testing apparatus. Flow meters with a sufficient gas flow rate encompassing maximum nostril performance may also be used.

In addition to actually testing the relative airflow of the nostrils, the following items need to be considered in establishing a clinically acceptable baseline of nasal performance and the appropriateness of testing a particular patient with the disclosed devices, systems and methods.

A medical history of the patient may be obtained in regard to injury to the nose, the individual nostrils and associated airways and inhalation performance thereof, known or observed structural abnormalities, significant nose bleeds, a history of sinus infections, known strokes or T.I.A.s, current nasal congestion, a diagnosis of deviated septum, any previous nasal surgery, nasal tumors, polyups, allergies, a history of exposure to strong industrial odors, age, etc., to enhance the clinical significance of the results of the present invention and, potentially, to disqualify certain individuals from taking the test.

An illuminated optical examination of the nasal passage may be executed to identify mucous plugs, serious inflammation or other structural or medical impediments to a freely flowing nasal airway.

Administering a decongestant or other medicine to open airways may also be indicated in certain patient prior to nasal airflow measurements and aroma testing.

Retesting the subject at a later time of the same day or at later date may also mitigate temporary nasal conditions that might otherwise skew the test results.

A sliding scale, or corrective factor as described above, to mathematically adjust, or "handicap" the bilateral smelling acuity scores for a non-symmetrical baseline of nasal air flow may be applied to the aroma scale test results.

Cutoff levels will be established which will disqualify certain people from being considered a good candidate for the disclosed pure aroma detection test.

The disclosed aroma testing devices may be "tuned" in a number of ways during the industrial design process towards creating ideal efficacy as will be understood by the skilled artisan. For example, the diameter of the air intake ports, the diameter of gas supply tubes, the diameter of ports into and out of the aroma chamber, the size and diameter of the clear air chamber, the diameter of cannula tubes and disposable nasal cannula parts can be enlarged or constricted to achieve effective control of aroma concentration. Thus, time intervals or breaths may be adjusted as required to reach a threshold condition through scaling the apparatus. Electronic ultrasonic aroma emitters may also be adjusted to create a weaker or stronger aroma concentration.

The concentration of aroma may also be controlled by using various pure aroma producing materials and by controlling aroma dilution and the amount used. The surface area of the aroma chamber and surface area of the aroma source exposed to passing air are also controllable design variables. A minimum amount of aroma detectable is preferred, to reduce possible latency of aroma in what is intended to be substantially clear air. Coatings, filters and aroma absorbing elements may be applied to various embodiment to repel and/or absorb aroma molecules, thereby reducing latent aroma in what is intended to be substantially clear air.

Aroma sources as described herein may be in the form of a liquid held in an absorbent porous material such as a wick, stiff blotter slide or a cotton ball that is placed in the aroma chamber of the test apparatus. A viscous material such as peanut butter could be wiped onto a slide like element and inserted into the aroma chamber or the material supplied in a disposable portion package with removable seal top. Odorants, or pure odorants, may be used as discussed herein.

An ultrasonic USB powered aroma emitter may be employed as the aroma or odorant source. The advantages of using an ultrasonic device to generate aroma from an essential oil, is that such a device is turned on or off electronically by way of a momentary/normally off microswitch. Alternatively, a USB powered aroma emitter may be controlled by a computer device. Thus, the switching of the aroma source to be on or off may be computer controlled.

Such aroma/odorant diffusion devices are suitable to use as a cartridge that is inserted into the housing of the various devices as described herein. Such devices are refillable and may be filled with any essential oil. USB type ultrasonic devices emit little aroma when switched off. They may be used in the test devices of the present invention comprising, e.g., a single air chamber, thus reducing the complexity and parts required to manufacture such devices.

A disposable tank of a pure aroma or odorant or pure odorant infused breathable gas may be used some embodiments of the invention as described herein. Rather than simply using a ratio of smelling acuity as seen with aroma infused air, an aroma infused compressed gas in a disposable tank might offer a very specific aroma level measured in parts per million at the factory, which is may create very specific and repeatable test result using digital nose technology.

Repeating the testing protocol discussed herein a number of times, no matter which embodiment is used, with a randomized rotation between the nostrils and fully purging unscented airways between testing events, will create a meaningful and repeatably accurate and clinically acceptable test result.

As discussed above, the results from the use of the various embodiments of the devices, systems and methods of the present invention may be used to identify an asymmetry in a patient's olfactory threshold determined for the left and right airways. In the case of pure odorants used in the testing protocol, e.g., if an olfactory deficiency is detected via a higher olfactory threshold in the patient's left nostril and associated airway, this may provide early indication of Alzheimer's disease.

Alternatively, the results from the use of the various embodiments of the devices, systems and methods of the present invention may be used to identify an olfactory dysfunction, as compared with a baseline value, that is generally symmetrical as determined by the patient's olfactory threshold in the left and right airways. Once this type of dysfunction is determined, the patient's olfactory threshold may be monitored for several purposes including, but not limited to, monitoring the progress of the disease and/or condition contributing at least in part to the symmetrical olfactory dysfunction and/or monitoring the efficacy of a treatment regimen developed to treat the underlying disease, condition and/or olfactory dysfunction.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A nasal testing device for detecting a patient's pure odorant bilateral olfactory detection threshold for a nostril, comprising:
  a housing, the housing comprising:
    a pure odorant compartment within the housing and comprising a pure odorant within the pure odorant compartment;
    a left airway passage defined within the housing and in fluid communication with a clear air source and in switchable communication with the pure odorant compartment;
    a right airway passage defined within the housing and in fluid communication with the clear air source and in switchable communication with a pure odorant located within the pure odorant compartment;
    a left nasal tip having a lumen therethrough and in fluid communication with the left airway passage;
    a right nasal tip having a lumen therethrough and in fluid communication with the right airway passage;
    a left airway one-way valve in fluid communication with the lumen of the left nasal tip and the left airway passage and a right airway one-way valve in fluid communication with the lumen of the right nasal tip and the right airway passage, the left and right airway one-way valves allowing exhalation but not inhalation therethrough;
    a floating ball within the left airway; and a floating ball within the right airway, the floating balls adapted to indicate relative inhalation force, wherein the inhalation force through the left and right airways is generated exclusively from the patient's inhalation at the right and left nasal tips;
    a left airway activation switch, adapted to switch the left airway out of fluid communication with the clear air source into fluid communication with the pure odorant compartment, thereby introducing pure-odorant infused air into the left airway passage when the right airway remains in fluid communication with the clear air source;
    a right airway activation switch, adapted to switch the right airway out of fluid communication with the clear air source and into fluid communication with the pure odorant compartment, thereby introducing pure-odorant infused air into the right airway passage when the left airway remains in fluid communication with the clear air source,
  wherein the left airway activation switch is adapted to further switch the left airway passage out of fluid communication with the pure odorant compartment and into fluid communication with the clear air source when the right airway is switched into fluid communication with the pure odorant compartment; and
  wherein the right airway activation switch is adapted to further switch the right airway passage out of fluid communication with the pure odorant compartment and into fluid communication with the clear air source when the left airway is switched into fluid communication with the pure odorant compartment.

2. The device of claim 1, wherein the pure odorant is selected from the group consisting of: peanut butter, coffee, vanilla, cinnamon, and lavender.

3. The device of claim 1, wherein the clear air source is selected from the group consisting of: an air pump, a nebulizer, a compressed air device, and ambient air.

4. The device of claim 1, wherein each nasal tip forms a substantial seal with the patient's nostrils.

5. The device of claim 4, wherein each nasal tip is removable.

6. The device of claim 5, wherein each nasal tip comprises a disposable nasal specula tip.

7. The device of claim 1, wherein the clear air source is ambient air and a flow of clear air through the clear airway passage is initiated by the force of the patient's inhalation of clear air through the clear airway passage.

8. The device of claim 1, wherein the first and second nasal tips each form a seal with one of the patient's nostrils.

9. The device of claim 1, further comprising an ultrasonic aroma emitting source disposed within the pure odorant compartment and in operative connection with a power source, the ultrasonic aroma emitting source in operational communication with the left and right airway passages sequentially and adapted to emit pure odorant aromas only that stimulate the first cranial nerve but not the fifth cranial nerve, without emission of odorants that stimulate at least the fifth cranial nerve.

10. The device of claim 1, wherein the first and second nasal tips are color coded.

11. The device of claim 1, wherein the device is controlled by, and in two-way communication with, a programmable computing device.

12. The device of claim 11, wherein the programmable computing device comprises a software application having a time keeping function, a results database, a random nostril event and odorant generator, and a remote server in communication with the programmable computing device and comprising a memory and a processor in communication with the memory with programmed instructions stored therein adapted to generate a test score based on test trial data obtained for each nostril.

13. The device of claim 1, further comprising the left and right airway passages comprising a coating that repels the pure odorant molecules.

* * * * *